US010977495B2

(12) United States Patent
Hares et al.

(10) Patent No.: US 10,977,495 B2
(45) Date of Patent: Apr. 13, 2021

(54) AUTOMATIC ENDOSCOPE VIDEO AUGMENTATION

(71) Applicant: CMR SURGICAL LIMITED, Cambridge (GB)

(72) Inventors: Luke David Ronald Hares, Cambridge (GB); Paul Christopher Roberts, Cambridge (GB); Rupert Menzies, Cambridge (GB); Mark Clifford Slack, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 0 days.

(21) Appl. No.: 16/591,779

(22) Filed: Oct. 3, 2019

(65) Prior Publication Data

US 2020/0110936 A1    Apr. 9, 2020

(30) Foreign Application Priority Data

Oct. 3, 2018    (GB) .................................. 1816164.6

(51) Int. Cl.
*G06K 9/00*    (2006.01)
*A61B 34/30*   (2016.01)
(Continued)

(52) U.S. Cl.
CPC ...... *G06K 9/00671* (2013.01); *A61B 1/00009* (2013.01); *A61B 1/00045* (2013.01);
(Continued)

(58) Field of Classification Search
CPC ............ A61B 1/00009; A61B 1/00045; A61B 1/0005; A61B 1/00149; A61B 1/3132;
(Continued)

(56) References Cited

U.S. PATENT DOCUMENTS

2009/0081959 A1\*  3/2009  Gyorfi .................... H04L 67/18
                                                                  455/70
2013/0038707 A1    2/2013  Cunningham et al.
(Continued)

FOREIGN PATENT DOCUMENTS

EP          1504712 A1    2/2005
KR       100957470 B1     5/2010
(Continued)

OTHER PUBLICATIONS

Henry C. Lin et al: "Towards automatic skill evaluation: Detection and segmentation of robot-assisted surgical motions", Computer Aided Surgery, vol. 11, No. 5, Jan. 1, 2006 (Jan. 1, 2006), pp. 220-230, XP055651113, US, ISSN: 1092-9088, DOI: 10.3109/10929080600989189.

(Continued)

*Primary Examiner* — Sae Won Yoon
(74) *Attorney, Agent, or Firm* — Lando & Anastasi, LLP

(57) ABSTRACT

Methods and systems for automatically augmenting an endoscope video for a task based on status data that describes the status of a surgical robot system that was used to at least partially perform the task. The system comprises an event detector and an augmenter. The event detector is configured to: receive the status data; and identify one or more patterns in the status data that indicate an event occurred during the task. The augmenter is configured to receive an endoscope video captured during the task, the endoscope video being time synchronised with the status data; and in response to the event detector identifying a pattern in the status data that indicates an event occurred, automatically augment metadata that forms part of or is associated with the endoscope video with information identifying the event and the time the event occurred with respect to the endoscope video.

19 Claims, 13 Drawing Sheets

(51) Int. Cl.
*A61B 1/00* (2006.01)
*A61B 5/024* (2006.01)
*A61B 5/1455* (2006.01)
*A61B 17/04* (2006.01)

(52) U.S. Cl.
CPC ...... *A61B 1/00149* (2013.01); *A61B 5/02427* (2013.01); *A61B 5/14552* (2013.01); *A61B 17/0469* (2013.01); *A61B 34/30* (2016.02); *G06K 9/00718* (2013.01); *A61B 2034/301* (2016.02); *G06K 2009/00738* (2013.01)

(58) Field of Classification Search
CPC ............ A61B 5/02427; A61B 5/14552; A61B 17/0469; A61B 34/00; A61B 34/10; A61B 34/20; A61B 34/25; A61B 34/30; A61B 90/36; A61B 90/37; A61B 90/90; A61B 2034/301; G06K 9/00671; G06K 9/00711; G06K 9/00718; G06K 2009/00738; G06K 2209/05; G06K 2209/27; G06T 7/0012; G06T 19/006; G06T 2207/10068
USPC ........................................................ 345/632
See application file for complete search history.

(56) References Cited

U.S. PATENT DOCUMENTS

| | | |
|---|---|---|
| 2014/0031659 A1 | 1/2014 | Zhao et al. |
| 2014/0275760 A1 | 9/2014 | Lee et al. |
| 2015/0157411 A1* | 6/2015 | Choi ...................... A61B 34/37 606/130 |
| 2015/0366628 A1 | 12/2015 | Ingmanson |
| 2016/0322078 A1* | 11/2016 | Bose ...................... A63F 13/217 |
| 2017/0039423 A1* | 2/2017 | Cork .................. G02B 27/0172 |
| 2017/0094219 A1* | 3/2017 | Kim ........................ G11B 27/30 |
| 2017/0304007 A1 | 10/2017 | Piron et al. |
| 2018/0047429 A1* | 2/2018 | Smith ................ H04N 21/8456 |
| 2018/0092706 A1 | 4/2018 | Anderson et al. |
| 2018/0197624 A1* | 7/2018 | Robaina ................. G16H 10/60 |
| 2019/0362834 A1* | 11/2019 | Venkataraman ....... G16H 30/40 |
| 2019/0374220 A1* | 12/2019 | Fischell ........... A61B 17/06109 |

FOREIGN PATENT DOCUMENTS

| | | |
|---|---|---|
| KR | 20100106834 A | 10/2010 |
| WO | 2018067611 A1 | 4/2018 |

OTHER PUBLICATIONS

Notification of Transmittal of the International Search Report and the Written Opinion of the International Searching Authority from corresponding PCT/GB2019/052801 dated Dec. 18, 2019.

United Kingdom Search Report from corresponding United Kingdom Application No. GB1816164.6 dated Mar. 28, 2019.

* cited by examiner

AUTOMATIC ENDOSCOPE VIDEO AUGMENTATION

CROSS-REFERENCE TO RELATED APPLICATION

This application claims the benefit under 35 U.S.C. § 119 of United Kingdom Patent Application No. 1816164.6 filed on Oct. 3, 2018 which is hereby incorporated herein by reference in its entirety for all purposes.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

The surgical robot 100 is controlled remotely by an operator (e.g. surgeon) via an operator console 200 shown in FIG. 2. The operator console 200 may be located in the same room (e.g. operating theatre) as the surgical robot 100 or remotely from it. The operator console 200 comprises input devices 202, 204 for controlling the state of the arm 102 and/or instrument 105 attached thereto. The input devices 202, 204 may be handgrips or hand controllers mounted on parallelogram linkages. A control system converts the movement of the hand controllers into control signals to move the arms joints and/or instrument end effector of a surgical root. The operator console 200 also comprises a display 206. The display 206 is arranged to be visible to a user operating the input devices 202, 204. The display is used to display a video stream of the surgical site (e.g. endoscope video).

Some surgical procedures may require several surgical robots, each one carrying an instrument or other implement which is used concurrently with the others at the surgical site. FIG. 3 illustrates a surgical robot system 300 with multiple robots 302, 304, 306 operating in a common workspace on a patient 308. For example, surgical robots are often used in endoscopic surgery (e.g. laparoscopic surgery), which also may be referred to as minimally invasive surgery. As is known to those of skill in the art, during an endoscopic procedure the surgeon inserts an endoscope through a small incision or natural opening in the body, such as, but not limited to, the mouth or nostrils. An endoscope is a rigid or flexible tube with a tiny camera attached thereto that transmits real-time images to a video monitor (e.g. display 206) that the surgeon uses to help guide his tools through the same incision/opening or through a different incision/opening. The endoscope allows the surgeon to view the relevant area of the body in detail without having to cut open and expose the relevant area. This technique allows the surgeon to see inside the patient's body and operate through a much smaller incision than would otherwise be required for traditional open surgery. Accordingly, in a typical robotic endoscopic surgery there is an endoscope attached to one surgical robot arm and one or more surgical instruments, such as a pair of pincers and/or a scalpel, attached to one or more other surgical robot arms.

FIG. 4 illustrates an example endoscope 400 which is attachable to the end of a robot arm for use in minimally invasive surgery. The endoscope 400 has a distal end 402 for insertion into the surgical site of the patient, and a proximal end 404. The distal end 402 is connected to the proximal end 404 by an elongate shaft 406. The proximal end 404 comprises an interface 408 for engaging the end of the robot arm.

The endoscope 400 has a power source and a light source for illuminating the surgical site. The endoscope 400 also has a data line for extracting the image data from the surgical site. These may all be attached to the proximal end 404 of the endoscope 400 independently and externally of the robot arm, as shown in FIG. 4. In FIG. 4, power is applied through stem 412, image data is extracted through stem 412, and light is applied through light stem 410. In an alternative implementation, any one or more of the light input, power input and data output may be applied/extracted to the endoscope through the robot arm.

The endoscope 400 mounts to the end of the robot arm. The endoscope interface 408 engages a complementary interface of the robot arm. The endoscope 400 is attachable to and detachable from the robot arm via the robot arm and endoscope interfaces. In some cases, the endoscope 400 is operable independently of the robot arm in its detached state. In other words, in these cases the endoscope 400 can be operated manually by a member of the operating room staff when detached from the robot arm.

In addition to the images captured by the endoscope (which may be collectively referred to herein as the endoscope video) being used during surgery, the images captured by the endoscope may be recorded and subsequently used for a variety of purposes such as, but not limited to, learning and/or teaching surgical procedures, and assessing and/or reviewing the performance of the surgeon (by a third party or by the surgeon himself/herself).

One of the advantages of robot assisted surgery over conventional manual surgery is that it permits data to be gathered more easily about how surgical procedures are performed. For example, the motion and/or position of the robot(s) during surgery can be monitored and logged. It would be advantageous to be able to link or otherwise connect the endoscope video with the data generated/collected by, or about, the surgical robot(s) to improve the usefulness of the endoscope video in teaching, performance assessment/review etc.

The embodiments described below are provided by way of example only and are not limiting of implementations which solve any or all of the disadvantages of known surgical robot systems.

SUMMARY

This summary is provided to introduce a selection of concepts that are further described below in the detailed description. This summary is not intended to identify key features or essential features of the claimed subject matter, nor is it intended to be used to limit the scope of the claimed subject matter.

Described herein are methods and systems for automatically augmenting an endoscope video for a task at least partially performed by a surgical robot system based on status data that describes the status of the surgical robot system during the task. The system comprises an event detector and an augmenter. The event detector is configured to: receive the status data; and identify one or more patterns in the status data that indicate an event occurred during the task. The augmenter is configured to: receive an endoscope video captured during the task, the endoscope video being time synchronised with the status data; and in response to the event detector identifying a pattern in the status data that indicates an event occurred, augment metadata that forms part of or is associated with the endoscope video with information identifying the event and the time the event occurred with respect to the endoscope video.

A first aspect provides an augmentation system to generate an augmented endoscope video, the augmentation system comprising: an event detector configured to: receive status data describing a status of a surgical robot system during a task at least partially performed by the surgical robot system, the surgical robot system comprising at least one surgical robot having a base, and an arm extending from the base to an attachment for an instrument, the arm comprising a plurality of joints whereby the configuration of the arm can be altered; and identify one or more patterns in the status data that indicate an event occurred during the task; and an augmenter configured to: receive an endoscope video captured during the task, the endoscope video being time synchronised with the status data; and in response to the event detector identifying a pattern in the status data that indicates an event occurred, automatically augment metadata that forms part of or is associated with the endoscope video with information identifying the event and the time of the event with respect to the endoscope video.

The information identifying the event and the time of the event may be visible to a user when the augmented endoscope video is subsequently viewed by the user.

The information identifying the event and the time of the event may be selectively visible to a user when the augmented endoscope video is subsequently viewed by the user.

The information identifying the event and the time of the event may be automatically viewable or not viewable to a user when the augmented endoscope video is subsequently viewed by the user based on privileges associated with the user.

Augmenting the metadata with information identifying the event and the time of the event with respect to the endoscope video may comprise adding a bookmark to the endoscope video at the time of the event that identifies the event.

The one or more patterns may comprise a plurality of patterns, each pattern corresponding to a different event, and the event detector may be configurable to selectively identify only a subset of the plurality of patterns.

The one or more patterns may comprise a plurality of patterns, each pattern corresponding to a different event and the event detector may be configured to identify a subset of the plurality of patterns based on user privileges associated with a user that initiated the augmentation.

The status data may at least partially comprise data generated by the surgical robot system.

The status data may at least partially comprise data generated by one or more sources external to the surgical robot system The one or more patterns may be configured to identify one or more instrument events, the one or more instrument events may comprise one or more of: a change in at least one instrument attached to an arm of the surgical robot system; a change in a status of an energised instrument attached to an arm of the surgical robot system; cleaning of an endoscope attached to an arm of the surgical robot system; performing a white balance on an imaging system of an endoscope attached to an arm of the surgical robot system; a size or frequency of movement of an endoscope attached to an arm of the surgical robot system falling outside a range; and a change in at least one instrument attached to an arm of the surgical robot system being actively controlled by the surgical robot-system.

The one or more patterns may be configured to identify one or more collision events, the one or more collision events may comprise one or more of: a collision between at least two surgical robot arms of the surgical robot system; a collision between at least two instruments attached to different surgical robot arms of the surgical robot system; and a collision between a surgical robot arm of the surgical robot system and an instrument attached to another surgical robot arm of the surgical robot system.

The task may be a surgical procedure performed on a patient and the one or more patterns may be configured to identify one or more patient events, the one or more patient events may comprise one or more of: one or more vital signs or one or more other health metrics of the patient falling outside a range; and a change in one or more vital signs and/or one or more other health metrics of the patient.

The surgical robot system may be controlled by an operator, and the one or more patterns may be configured to identify one or more operator events, the one or more operator events may comprise one or more of: one or more vital signs and/or one or more other health metrics of the operator falling outside a range; a change in one or more vital signs and/or one or more other health metrics of the operator; a change in a grip force exerted by the operator on one or more input devices used to control the surgical robot system; and a change in a push force exerted by the operator on one or more of the input devices.

The surgical robot system may be controlled by an operator, and the one or more patterns may be configured to identify one or more operator performance events, the one or more operator performance events may comprise one or more of: a performance of the operator in performing the task falling below an acceptable level, and a change in the performance of the operator in performing the task.

The performance of the operator in performing the task may be based on one or more performance criteria, the one or more performance criteria may comprise one or more of: a path taken by a surgical robot arm in performing a step of the task; a smoothness of the surgical robot arm; and a duration to complete a step of the task.

The one or more patterns may be configured to identify emergency events.

The task may comprise a plurality of steps and the one or more patterns may be configured to automatically identify the one or more steps of the task from the status data.

The status data may comprise instrument information describing instruments attached to the at least one surgical robot during the task and surgical robot position information describing a movement and/or a position of the at least one surgical robot during the task; and the event detector may be configured to identify a suturing step in the task by identifying patterns in the instrument information and the surgical robot position information.

The event detector may be configured to identify a suturing step in the task when the event detector identifies from the instrument information that at least two needle drivers are attached to surgical robots and the event detector identifies from the surgical robot position information that the surgical robots were moved in repeated circular motions.

The system may be further configured to link the augmented endoscope video and all or a portion of the status data so that the information identifying an event identifies the time the event occurred with respect to the endoscope video and the status data.

A portion of the endoscope video and a portion of the status data relating to an identified event may be retrievable from the information identifying the event The task may be a surgical procedure performed on a human.

The augmentation system may comprise the surgical robot system.

A second aspect provides a computer-implemented method of generating an augmented endoscope video, the method comprising, at one or more computing-based devices: receiving an endoscope video captured during a task at least partially performed by a surgical robot system, the surgical robot system comprising at least one surgical robot having a base, and an arm extending from the base to an attachment for an instrument, the arm comprising a plurality of joints whereby the configuration of the arm can be altered; receiving status data describing a status of the surgical robot system during the task, the status data being time synchronised with the endoscope video; identifying one or more patterns in the status data that indicate an event occurred during the task; and in response to identifying a pattern in the status data that indicates that an event occurred during the task, augmenting metadata that forms part of or is associated with the endoscope video with information identifying the event and the time of the event with respect to the endoscope video.

The above features may be combined as appropriate, as would be apparent to a skilled person, and may be combined with any of the aspects of the examples described herein.

BRIEF DESCRIPTION OF THE DRAWINGS

Examples will now be described in detail with reference to the accompanying drawings in which.

Figure 1:
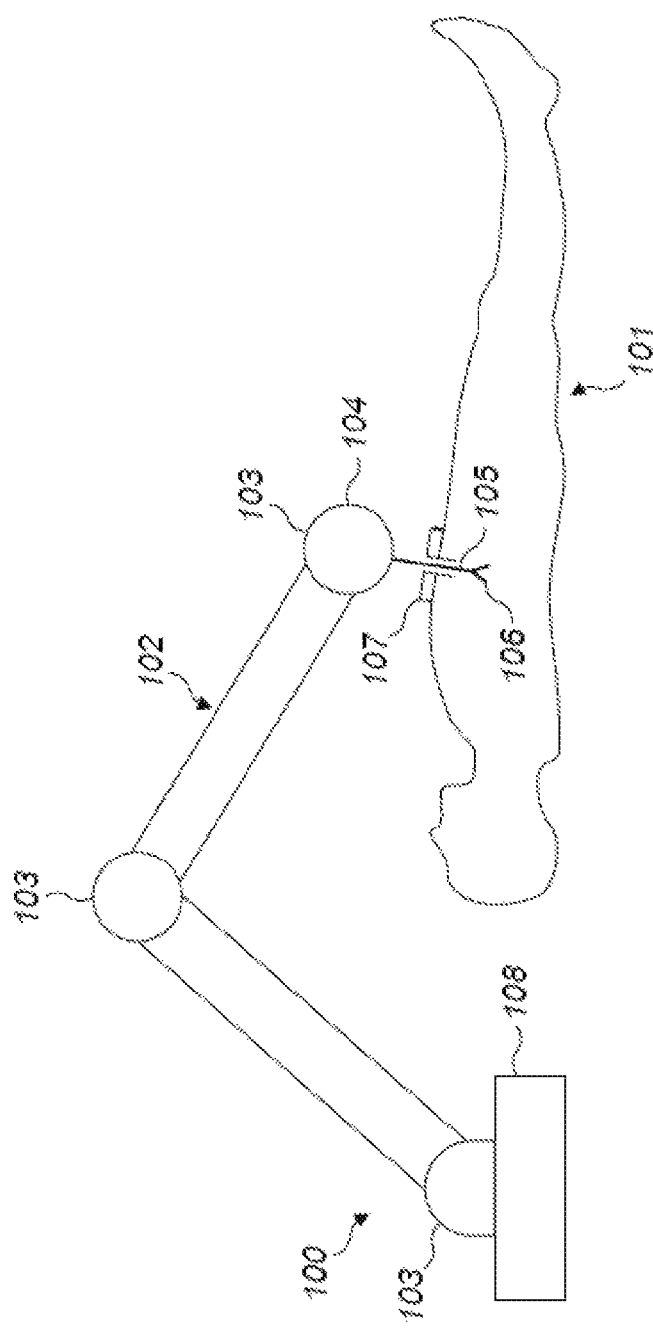
FIG. 1 is a schematic diagram of an example surgical robot performing an example surgical procedure.

The accompanying drawings illustrate various examples. The skilled person will appreciate that the illustrated element boundaries (e.g., boxes, groups of boxes, or other shapes) in the drawings represent one example of the boundaries. It may be that in some examples, one element may be designed as multiple elements or that multiple elements may be designed as one element. Common reference numerals are used throughout the figures, where appropriate, to indicate similar features.

DETAILED DESCRIPTION

The following description is presented by way of example to enable a person skilled in the art to make and use the invention. The present invention is not limited to the embodiments described herein and various modifications to the disclosed embodiments will be apparent to those skilled in the art. Embodiments are described by way of example only.

Described herein are methods and systems for automatically augmenting an endoscope video captured during a task (e.g. surgery) at least partially performed by a surgical robot system based on status data describing the status of the surgical robot system during the task. The surgical robot system comprises at least one surgical robot having a base, and an arm extending from the base to an attachment for an instrument wherein the arm comprises a plurality of joints whereby the configuration of the arm can be altered. The method comprises receiving the endoscope video; receiving status data describing the status of the surgical robot system during the task that is time synchronised with the endoscope video; identifying one or more patterns in the status data that indicate an event occurred during the task; and in response to identifying a pattern in the status data that indicates an event occurred, augmenting the endoscope video with information that identifies the event and the time of the event with respect to the endoscope video.

Figure 5:
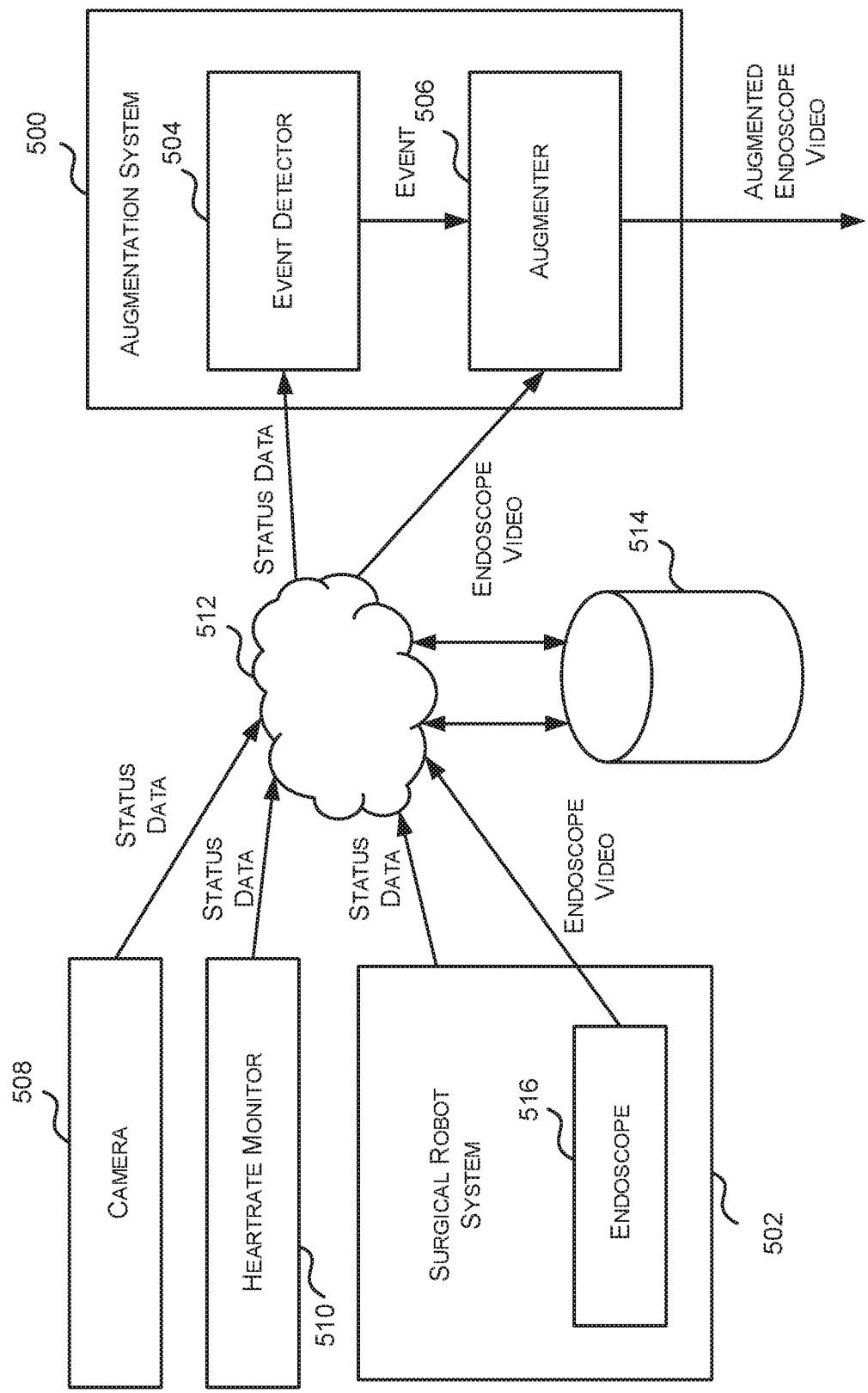
FIG. 5 is a block diagram of an example augmentation system.

Reference is first made to FIG. 5 which illustrates an example augmentation system 500 for automatically augmenting an endoscope video captured during a task (e.g. surgery) at least partially performed by a surgical robot system 502. The surgical robot system 502 comprises at least one surgical robot having a base, and an arm extending from the base to an attachment for a surgical instrument, the arm comprising a plurality of joints whereby the configuration of the arm can be altered. An example surgical robot system 502 is described below with reference to FIG. 6.

The augmentation system 500 comprises an event detector 504 and an augmenter 506. The event detector 504 and/or the augmenter 506 may be implemented by one or more computing-based devices, such as, but not limited to the example computing-based device described below with reference to FIG. 13.

The event detector 504 is configured to receive status data that indicates or describes the status of the surgical robot system 502 during the robotic task (e.g. surgery). The status data is time synchronised to the endoscope video captured during the task. The status data may be time synchronised to the endoscope video in any suitable manner that allows events detected from the status data to be correlated to a particular time or period of time in the endoscope video. For example, both the endoscope video and the status data may include, or be linked to, common timestamps or a common timeline.

As described in more detail below, the status data may comprise any data or information about the surgical robot system 502 and/or any information about the environment in which the surgical robot system 502 was operating during the task. All or a portion of the status data may be generated by the surgical robot system 502 itself (e.g. data relating to the position and/or movement of the surgical robot arm(s), instrument attached thereto, and any hand controllers that control the movement of the robot arm(s)). In some cases, at least a portion of the status data may be generated by one or more external sources.

For example, as shown in FIG. 5 a portion of the status data may be generated by audio and/or video recording equipment, such as, but not limited to, a camera 508, which captures audio and/or video in the room (e.g. operating theatre) in which the task is performed; and/or health monitoring equipment, such as, but not limited to, a heartrate monitor 510, which monitors one or more health metrics of the patient (if the task is performed on a patient) and/or the operator (e.g. surgeon) controlling the surgical robot system 502. It will be evident to a person of skill in the art that these are only examples of external sources of status data and there may be other external sources of status data. For example, other external sources of status data may include the patient bed, where the patient bed is a 'smart' bed that is able to generate, for example, position data; and insufflation equipment. As is known to those of skill in the art, during laparoscopic surgery, gases, such as, but not limited to carbon dioxide, are often insufflated into a body cavity via insufflation equipment to inflate the cavity for more workroom.

The event detector 504 may receive the status data generated by the surgical robot system 502 and/or the one or more external sources 508, 510 via any suitable means. For example, in some cases the surgical robot system 502 and/or one or more of the external sources 508, 510 may provide the status data to the event detector 504 via a wireless or wired communication connection 512 such as, but not limited to, an Ethernet connection, Wi-Fi® connection, Bluetooth® connection, Near-Field Communication (NFC) connection or the like. In these examples, all or a portion of the status data may be provided to the event detector 504 in real time (or in substantially real time) while the task (e.g. surgery) is being performed. In other cases, the status data may be captured by another device (e.g. a computing-based device) during the task and stored in a storage device 514 (e.g. memory) and subsequently provided to the event detector 504 via a communication connection 512 or via any other suitable means. In some cases, all or a portion of the status data may be stored, at the task location (e.g. operating theatre), on a portable storage medium, such as, but not limited to a USB (universal serial bus) memory stick, and physically transported to the location of the event detector 504 where it is coupled to the event detector 504 so that event detector 504 can read the status data from the portable storage medium.

The event detector 504 is configured to analyse the status data to identify events that occurred during the task (e.g. surgery). Events that occurred during the task (e.g. surgery) may include, but are not limited to: the instrument attached to a robot arm of the surgical robot system was changed; a collision occurred between multiple robot arms or between multiple instruments attached to robot arms; one or more of the patient's vital signs and/or one or more other patient health metrics have fallen outside a range; one or more of the operator's (e.g. surgeon's) vital signs and/or other operator health metrics have fallen outside a range; the surgical robot system 502 was used to perform a specific skill (e.g. suture); and a departure from the expected sequence events (e.g. a cutting step was performed when a suture step was expected). A more extensive list of example events that may be identified by the event detector 504 is described below. As described in more detail below, the event detector 504 may be configured to identify events that occurred during the task by identifying patterns in the status data. For example, the event detector 504 may be configured to determine that the surgical robot system 502 was used to perform a suture if the path taken by a robot arm or a needle instrument attached thereto indicates that a suture has been performed. The patterns that indicate that an event has occurred may be predetermined or may be learned from previously performed tasks.

In some cases, in response to detecting, from the status data, that an event occurred during the task (e.g. surgery) the event detector 504 may be configured to generate an output indicating that an event has been detected, the type of event, the time of the event and optionally the duration of the event which is provided to the augmenter 506.

The augmenter 506 is configured to receive an endoscope video captured by an endoscope 516 during the task. In some cases, the endoscope video may have been captured by an endoscope 516 attached to, and controlled by, one of the robot arms of the surgical robot system 502. However, in other cases, the endoscope video may have been captured by a manually controlled endoscope. For example, a user may be able to remove an endoscope attached to one of the robot arms and manually control the movement and operation of the endoscope. In some cases, when a user removes an endoscope from a robot arm and manually controls the endoscope the surgical robot system may no longer be able to accurately track the position and/or movement of the endoscope. As a result, the surgical robot system may be configured to limit the response to the control inputs while this is occurring.

The augmenter 506 may receive the endoscope video via any suitable means. For example, in some cases the endoscope 516 itself may be configured to provide the endoscope video to the augmenter 506 via a wireless or wired communication connection 512 such as not limited to, an Ethernet connection, a Wi-Fi® connection, a Bluetooth® connection, a Near-Field Communication (NFC) connection or the like. In these examples, all or a portion of the endoscope video may be provided to the augmenter 506 in real time (or in substantially real time) during the task (e.g. surgery). In other cases, the endoscope video may be stored in a storage device 514 (e.g. memory) and subsequently provided to the augmenter 506 via a communication connection 512 or via any other suitable means. For example, the endoscope video may be stored, at the location of the task (e.g. operating theatre) on a portable storage medium, such as, but not limited to a USB memory stick which is physically transported to the location of the augmenter 506 where it is coupled with the augmenter 506 so that the augmenter 506 can read the endoscope video from the portable storage medium.

The augmenter 506 is configured to, in response to the event detector 504 determining from the status data that an event occurred during the task, add information (e.g. a marker) to the endoscope video that identifies the event that occurred and when the event occurred, and optionally identifies the duration of the event, to generate an augmented endoscope video. In some cases, the information or marker may not be visible to a user when the augmented endoscope video is subsequently played or viewed in a video player. For example, in some cases the information or marker may be detectable by a special system or software. The special system or software may be configured to determine the identified events from the information or markers and present the user with a list of identified events. If a user selects one of the identified events the system may present or output the portion of the endoscope video relating to the identified event.

In other cases, the information or marker may be visible to the user when the augmented endoscope video is subsequently played or viewed in a video player. In some cases, the marker may take the form of a bookmark that allows a user to easily jump to a certain point of the endoscope video when the augmented endoscope video is played by a media player. For example, when the user launches the augmented endoscope video in a media player the user may be presented with a list of bookmarks in the video and the user can go directly to one of the points or sections identified by a bookmark by selecting the bookmark. In some cases, the augmenter 506 may be configured to automatically group the markers and/or bookmarks based on, for example, the type of event and/or any other criteria. In some cases, the augmenter 506 may also be configured to automatically identify additional events from the events identified via the status data and augment the endoscope video with an information/marker identifying each additional event. In some cases, the information (e.g. marker) relating to a particular event may be included in the metadata that forms part of or is associated with the endoscope video.

The augmentation system 500 may be remote from the surgical robot system 502. For example, the surgical robot system 502 may be located in an operating theatre and the augmentation system 500 may be in another room in the hospital or treatment centre.

Figure 2:
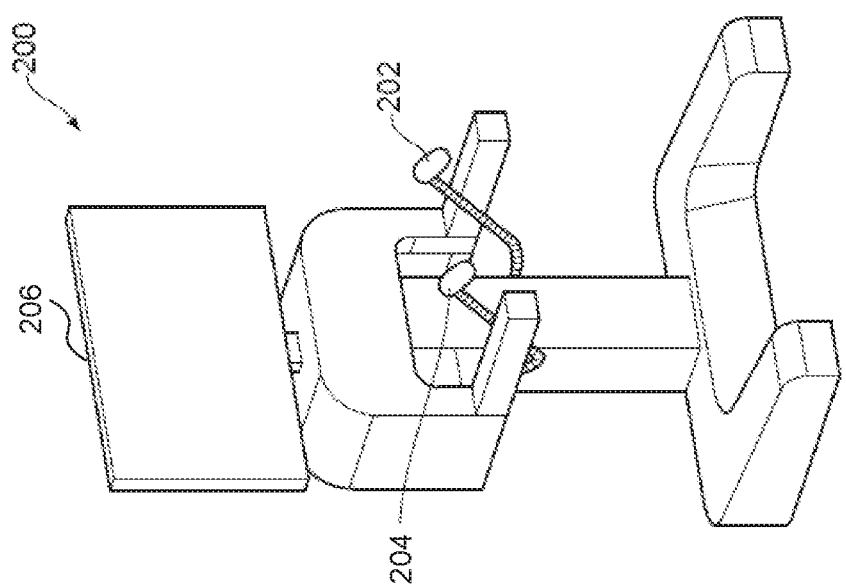
FIG. 2 is a schematic diagram of an example operator console.
Figure 3:
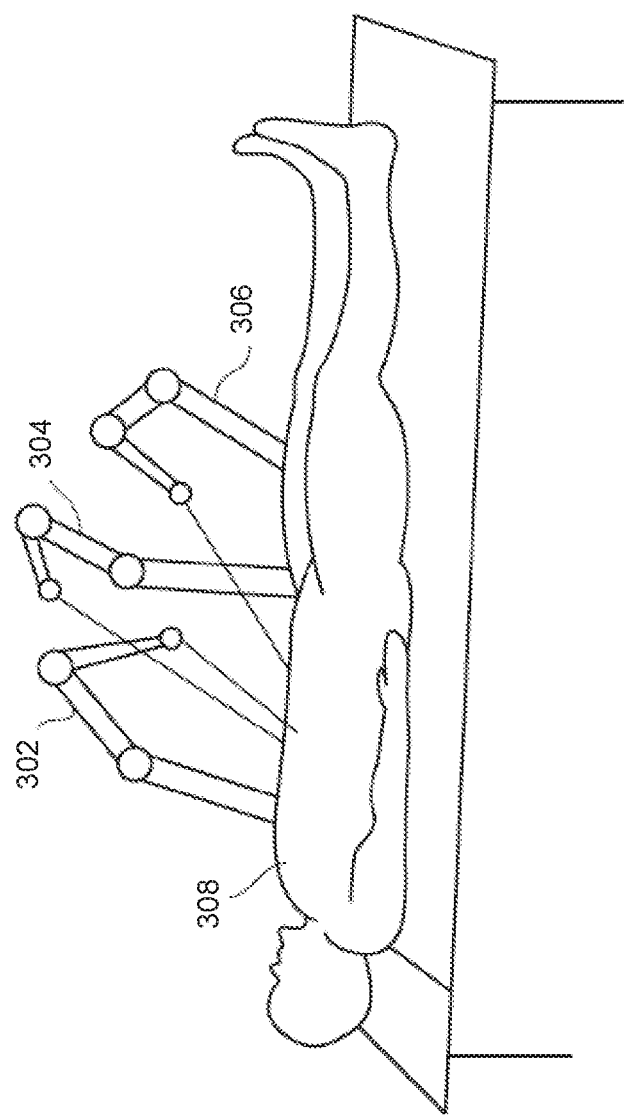
FIG. 3 is a schematic diagram of an example surgical robot system with a plurality of surgical robots.
Figure 4:
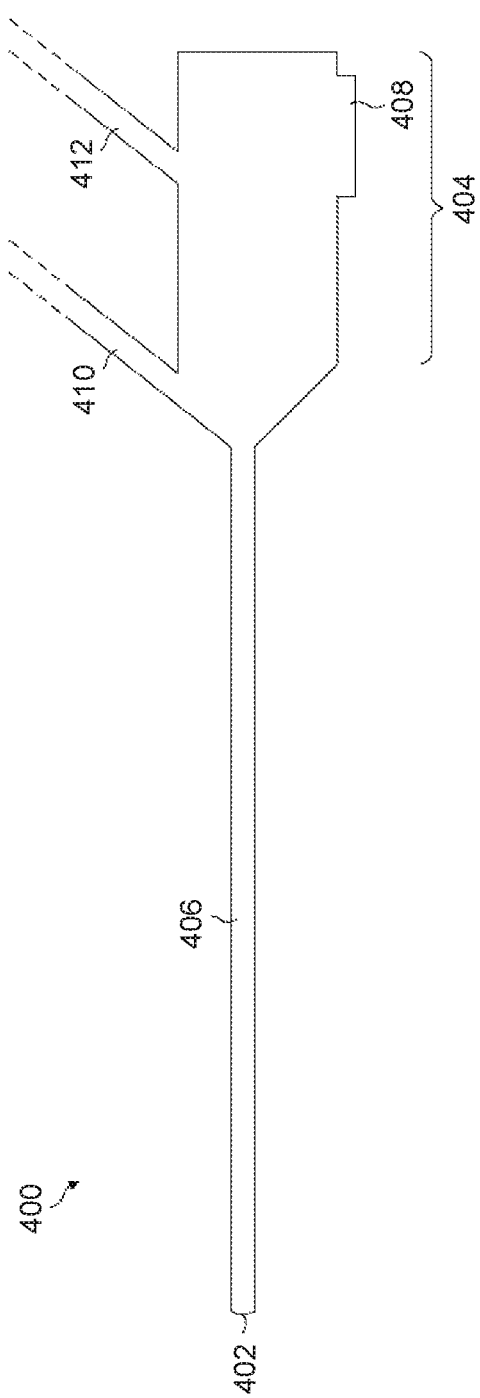
FIG. 4 is a schematic diagram of an example endoscope that is attachable to a surgical robot arm.
Figure 6:
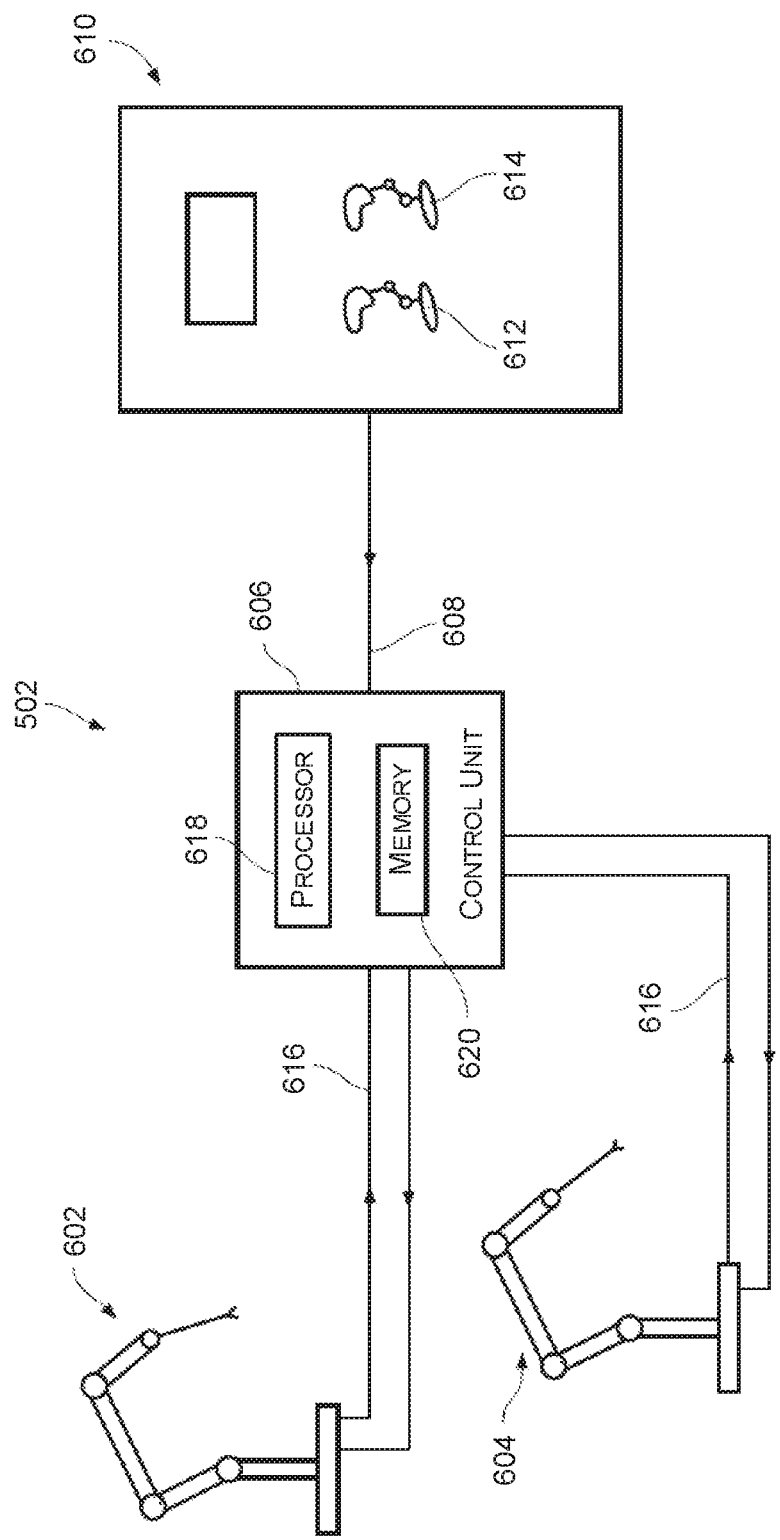
FIG. 6 is a schematic diagram of an example surgical robot system.

Reference is now made to FIG. 6 which illustrates an example surgical robot system 502. In this example the surgical robot system 502 comprises two surgical robots 602 and 604 driven by a control unit 606. The control unit 606 receives inputs 608 from an operator console 610 (such as, but not limited to the operator console 200 of FIG. 2), including inputs from first and second hand controllers 612, 614. The control unit 606 may receive other inputs from the operator console 610, such as foot pedal(s) inputs, voice recognition inputs, gesture recognition inputs, eye recognition inputs etc. The control unit 606 also receives inputs 616 from the surgical robots 602, 604. These inputs include sensor data from position sensors and torques sensors located on the robot arm joints. The control unit 606 may receive other inputs 616 from each robot, such as force feedback, data from or about the surgical instruments etc. The control unit 606 drives the robots 602, 604 in response to the inputs it receives from the robots 602, 604 and the operator console 610. The control unit 606 comprises one or more processors 618 and a memory 620. The memory 620 stores, in a non-transient way, software code that can be executed by the one or more processors 618 to control the drivers.

While the example surgical robot system 502 of FIG. 6 comprises two surgical robots, it will be evident to a person of skill in the art that the methods and techniques described herein are equally applicable to surgical robot systems with only one surgical robot and surgical robot systems with more than two surgical robots.

Figure 7:
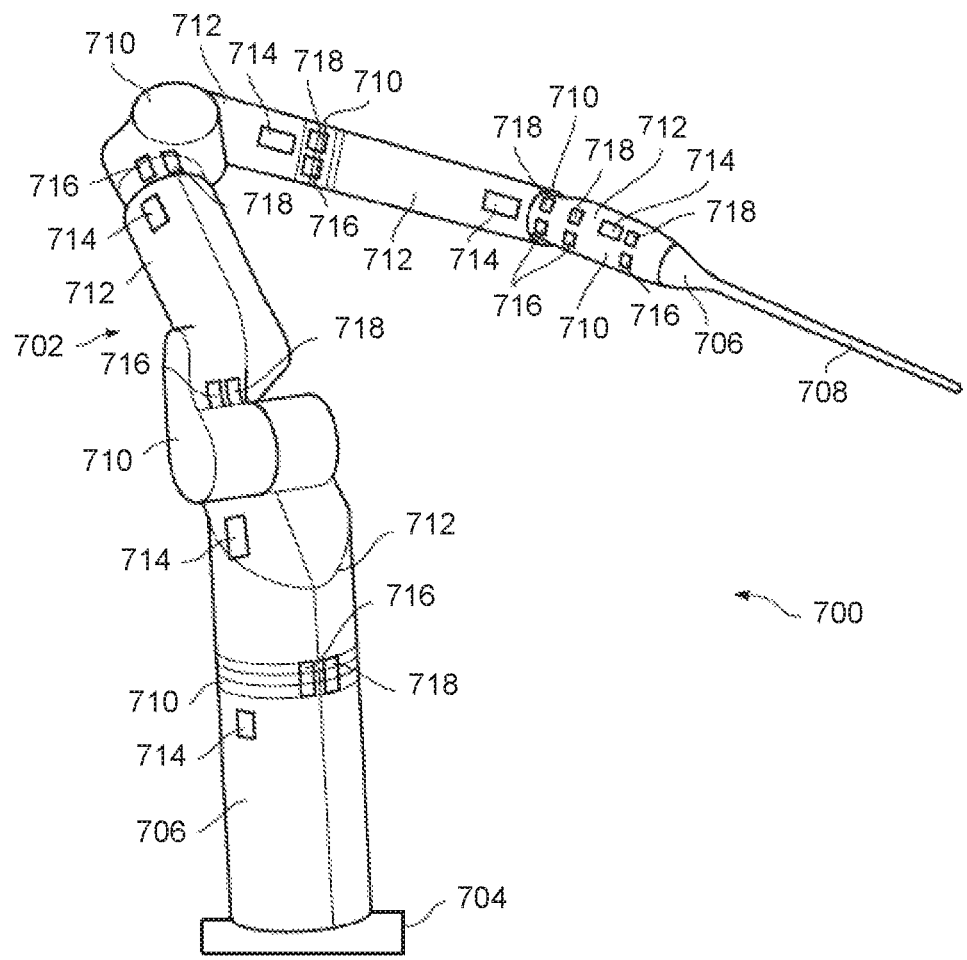
FIG. 7 is a schematic diagram of an example surgical robot.

Reference is now made to FIG. 7 which illustrates an example implementation of a surgical robot 700. One or more of the surgical robots 602, 604 of FIG. 6 may be implemented as the surgical robot 700 of FIG. 7. The surgical robot 700 comprises an arm 702 which extends from a base 704 which is fixed in place when a task (e.g. surgical procedure) is being performed. In some cases, the base 704 may be mounted to a chassis. The chassis may be a cart, for example a bedside cart for mounting the robot at bed height. Alternatively, the chassis may be a ceiling mounted device, or a bed mounted device.

The arm 702 extends from the base 704 of the robot to an attachment 706 for a surgical instrument 708. The arm is flexible. It is articulated by means of multiple flexible joints 710 along its length. In between the joints are rigid arm members 712. The arm in FIG. 7 has seven joints. The joints include one or more roll joints (which have an axis of rotation along the longitudinal direction of the arm members on either side of the joint), one or more pitch joints (which have an axis of rotation transverse to the longitudinal direction of the preceding arm member), and one or more yaw joints (which also have an axis of rotation transverse to the longitudinal direction of the preceding arm member and also transverse to the rotation axis of a co-located pitch joint). However, the arm could be jointed differently. For example, the arm may have fewer or more joints. The arm may include joints that permit motion other than rotation between respective sides of the joint, for example a telescopic joint. The robot comprises a set of drivers 714, each driver 714 drives one or more of the joints 710.

The attachment 706 enables the surgical instrument 708 to be releasably attached to the distal end of the arm. The surgical instrument 708 has a linear rigid shaft and a working tip at the distal end of the shaft. The working tip comprises an end effector for engaging in a medical procedure. The surgical instrument may be configured to extend linearly parallel with the rotation axis of the terminal joint of the arm. For example, the surgical instrument may extend along an axis coincident with the rotation axis of the terminal joint of the arm. The surgical instrument 708 could be, for example, a cutting, grasping, cauterising or imaging device (e.g. endoscope).

The robot arm comprises a series of sensors 716, 718. These sensors comprise, for each joint, a position sensor 716 for sensing the position of the joint, and a torque sensor 718 for sensing the applied torque about the joint's rotation axis. One or both of the position and torque sensors for a joint may be integrated with the motor for that joint. The outputs of the sensors are passed to the control unit 606 where they form inputs for the one or more processors 618.

Figure 8:
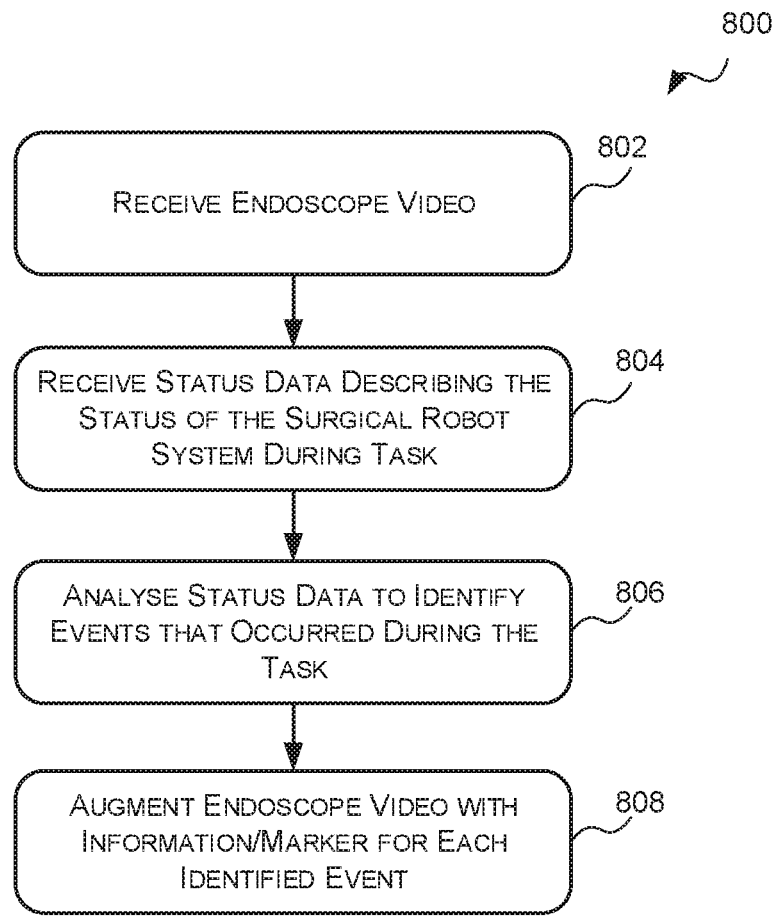
FIG. 8 is block diagram of an example method of augmenting an endoscope video.

Reference is now made to FIG. 8 which illustrates an example method 800 for automatically augmenting an endoscope video captured during a task (e.g. surgery) that was at least partially performed by a surgical robot system 502 based on status data describing the status of the surgical robot system during the task. Specifically, in the method 800 events that occurred during the task are detected from the status data, and the endoscope video is augmented with information (e.g. one or more markers) that identifies the detected events and the time the events occurred with respect to the endoscope video.

The method 800 beings at block 802 where the augmentation system 500 (e.g. augmenter 506) receives the endoscope video that was captured by an endoscope during at task (e.g. surgery) that was at least partially performed by a surgical robot system 502. As described above, in some cases the endoscope video may have been captured by an endoscope attached to, and controlled by, one of the robot arms of the surgical robot system 502. In other cases, the endoscope video may have been captured by a manually operated endoscope. As described above, the endoscope video may be received at the augmentation system 500 (e.g. augmenter 506) via any suitable means. For example, the endoscope video may be provided directly to the augmentation system 500 (e.g. augmenter 506) by the endoscope via a wired or wireless communication connection (e.g. an Ethernet connection, a Wi-Fi® connection, a Bluetooth® connection, an NFC connection etc.). In other cases, the endoscope video may be stored in memory of another device and provided to the augmentation system 500 via the other device.

At block 804, the augmentation system 500 (e.g. event detector 504) receives status data that describes the status of the surgical robot system 502 during the task (e.g. surgery). The status data may comprise any information describing the surgical robot system 502 during the task (e.g. surgery) or describing the environment in which the surgical robot system 502 was operating. As described above, the status data is time synchronised with the endoscope video so that events detected from the status data can be correlated to a point, or period, of time in the endoscope video.

All or a portion of the status data may be generated by the surgical robot system 502 itself (e.g. the surgical robot system may generate data relating to the position and or movement of the surgical robot arm(s) and/or the instruments attached thereto). In some cases, a portion of the status data may be generated by one or more external sources. The status data may comprise one or more streams of data each of which is individually time synchronised with the endoscope video. The term "stream of data" is used herein to mean a set of data that was generated by the same source and describes the same feature of the surgical robot system 502. For example, as described above, each joint of the surgical robot system 502 may comprise a position sensor 716 for sensing the position of the joint, and a torque sensor 718 for sensing the torque about the joint rotation axis. The data generated by each position sensor 716 may be considered a stream of data. Similarly, the data generated by each torque sensor 718 may be considered a stream of data.

The status data may comprise information or data that describes the current state of the robot arm(s) of the surgical robot system such as, but not limited to, position and/or torque information that indicates the position and/or movement of the robot arm(s), or the joints thereof. In particular, the status data may comprise the position and/or torque data generated by the position and/or torque sensors 716, 718. For example, each position sensor 716 may report the joint angle of the joint it is sensing, and/or each torque sensor may report the torque acting on the joint it is sensing. It will be evident to a person of skill in the art that this is an example only and that the surgical robot(s) may comprise other sensors that provide information on the status of the robot arm(s).

The status data may also, or alternatively, comprise data or information that describes the state of the instruments attached to the robot arm(s). For example, the status data may comprise information identifying whether there is an instrument attached to the robot arm(s) and, if so, the type of instrument attached to the robot arm(s). In particular, the surgical robot system 502 may comprise means for detecting whether an instrument is attached to the arm (e.g. the surgical robot system may comprise an instrument engagement means such as that described in Applicant's published patent application GB 2552855 A which is herein incorporated by reference), and means for automatically detecting the type of instrument (e.g. each instrument may comprise an RFID or other component which is configured to automatically provide information on its identity to the surgical robot system when it is attached to a robot arm) and this information may be provided to the event detector 504 as status data. The status data may also, or alternatively, comprise information such as, but not limited to, position and/or torque information that indicates the position and/or movement of the instrument(s) attached to the robot arm(s). It will be evident to a person of skill in the art that this is an example only and that that the surgical robot or the instruments themselves may comprise other sensors that provide information of the status of the instruments.

Where at least one of the instruments attached to the robot arm(s) is an energised instrument such as, but not limited to, an electrocautery instrument or an electrosurgical instrument, which is energised by an electrical current to perform a surgical function (e.g. cauterising, cutting etc.), the status data may comprise information on the status of the energised instruments such as, but not limited to, whether or not the energised instrument is currently being energised, and if so, the waveform of the electrical current that is used to energise the instrument.

Where at least one of the instruments attached to the robot arm(s) is an endoscope, the status data may comprise information indicating the position, movement, status and/or field of view of the endoscope.

The status data may also, or alternatively, comprise data or information that describes the state of the operator input devices (e.g. hand controllers 612, 614) which are used to control the operation of the robot arms and instruments. As described above, the operator input devices could, for example, be manually operable mechanical input devices such as hand controllers or joysticks. In these cases, the status data may comprise data such as, but not limited to, position and/or torque data that indicates the position and/or movement of the input devices (e.g. hand controllers 612, 614). For example, one or more of the input devices may comprise a position sensor which is configured to sense the position of the input device, and/or torque sensor which is configured to sense the torque or force applied to the input device. In some cases, the hand controller may be mounted on parallelogram linkages via gimbals. In these cases, the linkages and/or gimbals may comprise position and/or torque sensors which measure the positions and torque of the joints of the linkage and/or gimbal. These measurements may then be provided to the augmentation system 500 (e.g. event detector 504) as status data.

In some cases, where the input devices are hand controllers, each hand controller may comprise one or more hand contact sensors, or the like, which are configured to detect whether a person's hand is in contact with the hand controller or gripping the hand controlling which indicates whether the hand controllers are in use. In these cases, the hand contact detection information generated by the hand contact sensor(s) may be provided to the augmentation system 500 (e.g. event detector 504) as status data. In some cases, where the input devices are hand controllers, each hand controller may also, or alternatively comprise one or more grip sensors which are configured to detect the grip force applied to the hand controller (i.e. how tightly the operator is gripping the hand controller). In these cases, the grip force information generated by the grip force sensor(s) may be provided to the augmentation system 500 (e.g. event detector 504) as status data. In some cases, the hand contact sensor(s) and the grip sensors may be the same sensor or otherwise integrated. In some cases, the operator may be equipped with motion sensors on his/her hands that detect the motion of the operator's hands. In these cases, the hand motion data generated by the hand motion sensor may be provided to the augmentation system 500 (e.g. event detector 504) as status data.

The status data may also, or alternatively comprise, information on the mode of operation of the surgical robot system 502. For example, in some cases the surgical robot system 502 may be able to operate in one of a plurality modes such as, but not limited to, an active mode in which the operator (e.g. surgeon) is controlling one or more of the robot arms to perform a task (e.g. surgery); a selection mode in which the operator (e.g. surgeon) is selecting or switching which robot arm(s) they are going to control from the operator console 610; and an instrument change mode in which at least one of the instruments attached to a robot arm is being removed, attached and/or changed. There may also be several types of active mode. For example, in some cases there may be an endoscope active mode in which the operator is controlling an endoscope attached to a robot arm and an instrument active mode in which the operator is controlling one or more other instruments attached to one or more robot arms. In these cases, the status data may comprise information on the current operating mode of the surgical robot system 502. It will be evident to a person of skill in the art that these are example modes of operation of a surgical robot system and that there may be additional or different modes of operation of the surgical robot system 502.

Where the task being performed is a surgical procedure performed on a patient, the status data may also, or alternatively, comprise data related to the patient. For example, the status data may comprise patient health information or data that describes the status of the patient's health during the task. For example, the status data may comprise information that describes the patient's vital signs (e.g. body temperature, pulse rate, respiration rate) or other health metrics (e.g. blood pressure, oxygen saturation, blood glucose/sugar) during the task (e.g. surgery). Typically, during surgery, the patient's vital signs and other health metrics are measured by special medical measurement equipment, such as, a heart rate monitor, a pulse oximeter, a continuous glucose monitor (CGM) device, and the like. In these cases, the medical measurement equipment may be configured to send the vital sign information or other patient metric information to the augmentation system 500 (e.g. event detector 504) via, for example, a communication network (e.g. a wired or wireless communication network).

However, in other cases, information on the patient's vital signs and/or other patient health metrics may be obtained in another manner. For example, in some cases the operating theatre in which the surgery is being performed may be equipped with a video and/or audio recording device and the vital sign data and/or other patient medical data may be obtained from the video and/or audio recording. For example, where the medical measurement equipment produces an audible representation of the measurement (e.g. a set of audible tones or "beeps") an estimate of the measurement may be obtained through analysis of the audio recorded by the video and/or audio recording device. In another example, where the medical measurement equipment visually displays a current or previous measurement, the measurement may be obtained through image analysis of the video recorded by the video recording device (e.g. the measurement may be read off the medical measurement equipment). In other cases, one or more of the patient's vital signs may be obtained from the endoscope video. For example, the patient's pulse rate or blood oxygenation level may be identified from the endoscope video through video analysis techniques. In particular, the patient's blood oxygenation level may be determined from the colour of the patient's blood. Determining the patient's vital signs or other health metrics from the endoscope video may be facilitated by illumination of the relevant part of the patient's body.

The status data may also, or alternatively, comprise other information related to the patient, such as, but not limited to demographic information such as age and weight, and other medical information such as previous scans (e.g. x-rays, MRIs), previous outcomes, medical history, diagnosis history and/or treatment plan.

In some cases, the status data may also comprise surgeon health information or data that describes the health of the operator (e.g. surgeon) controlling the surgical robot system. For example, the status data may comprise information or data that describes one or more vital signals (e.g. body temperature, pulse rate, respiration rate) and/or other health metrics (e.g. blood pressure) of the operator (e.g. surgeon) during the task (e.g. surgery). For example, in some cases, where the input devices are hand controllers the hand controllers may comprise sensors that measure the heart rate of the operator (e.g. surgeon), the shakiness of the operator's (e.g. surgeon's) movement, and/or the sweat rate of the operator (e.g. surgeon) and provide information or data related to the measured heart rate, shakiness and/or sweat rate to the event detector 504 as status data. In other cases, there may be external medical devices, or the like, that are configured to measure the vital signs or other health metrics of the operator (e.g. surgeon) during the task. As described above with respect to the patient vital signs and other health metrics, the medical devices that measure the operator's (e.g. surgeon's) vital signs or other health metrics may be configured to provide data on the measured metrics to the event detector 504 via, for example, a communication network, or an estimate of the measured metrics may be obtained through other means (e.g. by analysis of video and/or audio of the operating theatre).

As described above, in some cases the room (e.g. operating theatre) in which the task is being performed may be equipped with audio and/or video recording equipment to record the sound in the room and/or a visual image of the room while the task is being performed. In these cases, the status data may also, or alternatively, comprise the video and audio data captured by the audio and/or video recording equipment.

Figure 9:
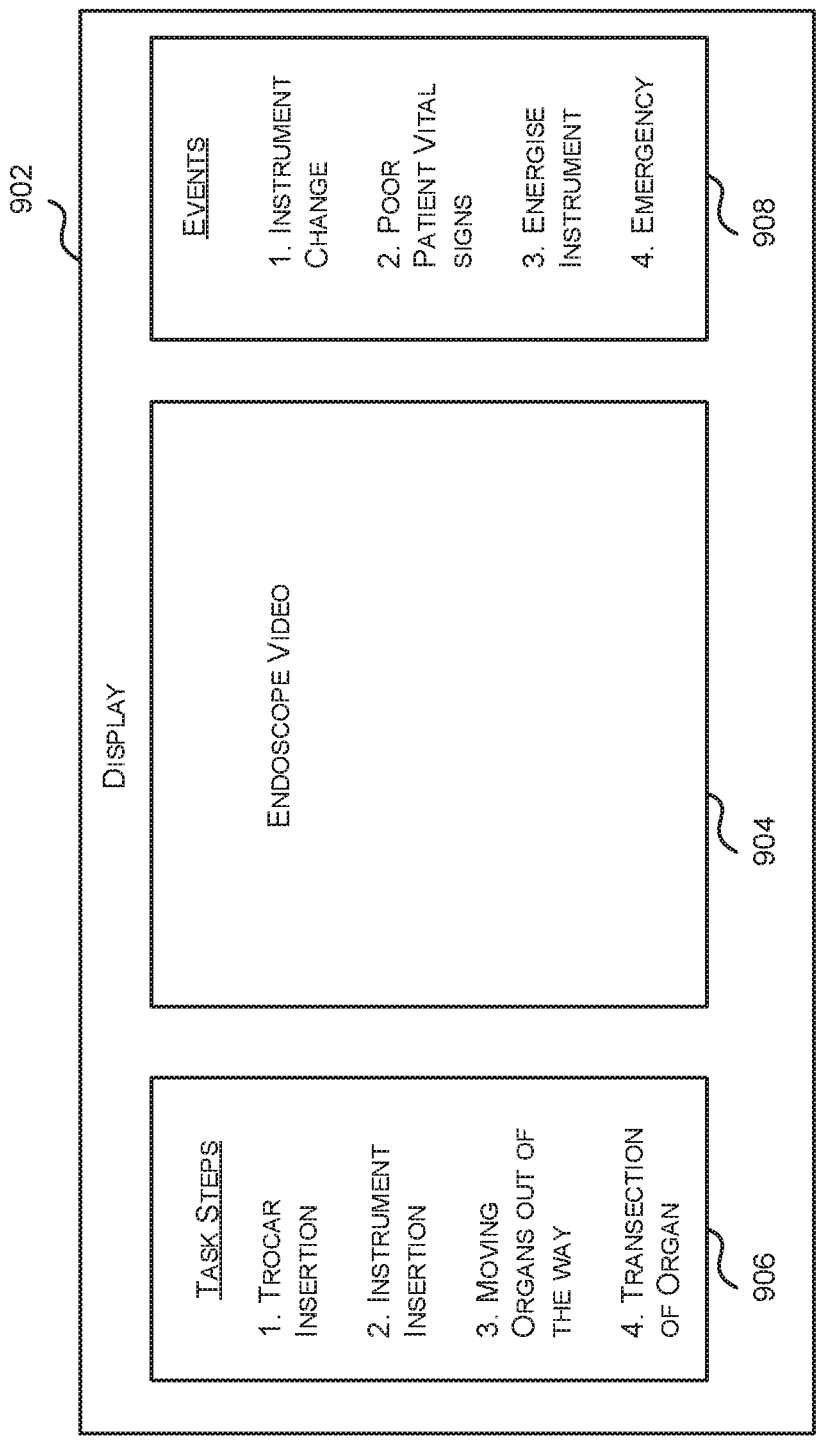
FIG. 9 is a schematic diagram of an example operator console display.

In some cases, the status data, may also, or alternatively, comprise information on the task being performed. For example, the status data may comprise information on the task (e.g. surgical procedure) that was at least partially performed by the surgical robot system 502. In some cases, where the task comprises a number of steps, the status data may comprise information indicating the steps of the task that were performed and when they were performed. For example, the operator (e.g. surgeon) of the surgical robot system 502 may be able to indicate during the task which step or phase of the task he/she is currently performing, and this information may be provided to the augmentation system 500 (e.g. event detector 504) as status data. For example, as shown in FIG. 9 the operator console 610 may comprise, or be associated with, a display 902 which displays the endoscope video 904 and also provides the operator with a list of the steps in the task 906. The listed steps may be automatically selected based on the task or may be manually entered by the operator (e.g. surgeon). For example, the operator (e.g. surgeon) may be able to manually enter the steps or phases of the task that the operator expects to execute. The operator (e.g. surgeon) may be able to select or otherwise indicate which of the listed steps or phases is currently being performed using the input devices (e.g. hand controllers 612, 614) by, for example, pressing a button on the hand-controller or via other means (e.g. verbally or via the display where the display is a touchscreen). Any selections made by the operator (e.g. surgeon) may then be provided to the augmentation system 500 (e.g. event detector 504) as status data.

In some cases, the status data may also, or alternatively, comprise information on the users of the surgical robot system 502 (e.g. the operator (e.g. surgeon) controlling the surgical robot(s) and/or other members of the task team (e.g. surgical team)). For example, in some cases, before the task is started, information may be provided to the surgical robot system 502 and/or the event detector 504 which indicates the users that will be performing the task. In other cases, the users (e.g. surgical team) performing the task (e.g. surgery) may be equipped with a device (e.g. RFID device, mobile telephone, tablet etc.) that may automatically transmit information to the surgical robot system 502 and/or the event detector 504 that identifies the user when they are in the vicinity of the surgical robot system. An example of such a system is described in the Applicant's co-pending UK patent application entitled "DEVICE INTEROPERATION" and filed the same day as the current application which is herein incorporated by reference.

In some cases, the operator (e.g. surgeon) controlling the surgical robot system, or another member of the task team (e.g. surgical team), may be able to manual indicate that an event has occurred. In particular, in some cases, the operator (e.g. surgeon) may be presented with a list of predetermined events that may occur during the task and the operator (e.g. surgeon) may be able to indicate that one of the predetermined events has occurred by selecting one of the predetermined events. Any selection(s) made by the operator (e.g. surgeon) may then be provided to the augmentation system 500 (e.g. event detector 504) as part of the status data. For example, as shown in FIG. 9. the operator console 610 may comprise, or may be associated, with a display 902 on which the endoscope video 904 is presented to the operator (e.g. surgeon). The display 902 may also display one or more predetermined events 908 that may occur during the task and the operator (e.g. surgeon) may indicate that one of the predetermined events has occurred by selecting one of the listed events. The predetermined events may be automatically selected based on the type of event, the particular operator and/or any other criteria; or the operator or another user may be able to manually enter a set of events that may occur during the task. In some cases, the augmentation system 500, or another computing-based device, may be configured to automatically generate, based on status data for previously performed tasks, high probability events or important events, for example, and it is these high probability events or important events that are presented to the operator (e.g. surgeon) as events that can be manually identified by the operator (e.g. surgeon) or other member of the task team.

The operator (e.g. surgeon) may be able to select one of the predetermined events using the input devices (e.g. hand controllers) by, for example, pressing a button on one of the hand controllers or via other means (e.g. verbally, or by touching the display 902 where the display 902 is a touchscreen). In other cases, another member of the task team (e.g. surgical team) may have a device, such as, but not limited to a computer or tablet, on which they are presented with a list of predetermined events and they can indicate that one of the predetermined events has occurred by selecting one of the predetermined events. Any selection may then be provided to the augmentation system 500 (e.g. event detector 504) as status data. An event that can be manually identified by the operator or another member of the task team may still be automatically detectable by the augmentation system from other status data.

Returning to FIG. 8, at block 806, the augmentation system 500 (e.g. event detector 504) analyses the status data to identify events that occurred during the task (e.g. surgery). The term "event" is used herein to mean the occurrence of an identifiable incident during the task. Events may include, but are not limited to, instrument events; collision events; task events; patient events; operator (e.g. surgeon) events; performance events; and/or emergency events. Examples of each of these types of events are described below.

The augmentation system 500 (e.g. event detector 504) may be configured to identify an event from the status data by identifying a pattern in the status data. One or more events may be identified by identifying a pattern in a single data stream of the status data or by identifying patterns in multiple streams of the status data. The augmentation system 500 is typically preconfigured with the pattern(s) that identify an event has occurred and which particular event that the pattern identifies. For example, the pattern(s) may be stored in memory of the augmentation system 500. The events and/or the specific pattern(s) that indicate an event has occurred may be manually determined or may be learned from the status data of previously performed tasks. For example, in some cases the augmentation system 500, or another computing-based device, may be configured to analyse status data of previously performed tasks which has been manually augmented with event information to identify common patterns in the status data that preceded identified events.

In some cases, the augmentation system 500 (e.g. event detector 504) may also, or alternatively, be configured to detect instrument events from the status data. Instrument events are those events that relate to the instruments used by (e.g. attached to) the surgical robot system 502 during the task. A surgical robot task (e.g. surgery) often requires a plurality of different surgical instruments. Multiple instruments may be used concurrently (e.g. there may be a plurality of robot arms to which a different instrument is attached and controlled thereby) and/or multiple instruments may be used sequentially (e.g. a first instrument may be attached to a robot arm to perform a specific function, that first instrument may be removed, and a second instrument is attached to that robot arm to perform a different function). An example set of instruments that may be using during a surgical robotic task may include, but it not limited to, scissors, graspers of a variety of forms and geometries, mono and bipolar electrosurgical instruments, other energy-driven instruments (e.g. laser or ultrasound instruments), a stapler, and a tissue sealer. Instrument events may include, but are not limited to, a change in at least one instrument attached to an arm of the surgical robot system; a change in the status of an energised instrument attached to an arm of the surgical robot system; cleaning of an endoscope attached to an arm of the surgical robot system; performing a white balance on the imaging system of an endoscope attached to an arm of the surgical robot system; the size or frequency of movement of an endoscope attached to an arm of the surgical robot system falls outside a range; and a change in at least one instrument attached to an arm of the surgical robot system being actively controlled by the surgical robot system.

As described above, the status data may comprise information that describes the state of instruments attached to the robot arm(s). For example, the status data may comprise information identifying whether an instrument is attached to each of the arm(s), the type of instrument attached to each robot arm, and where the instrument is an energised instrument the status of the energised instrument (e.g. whether the instrument is energised or not and, optionally the waveform of the electrical current supplied to the energised instrument. In these cases, the augmentation system 500 (e.g. event detector 504) may be configured to detect an instrument change event when it detects that an instrument was detached from a robot arm or if an instrument was attached to the arm. In these cases, the augmentation system 500 (e.g. event detector 504) may be configured to detect a change in the status of the energised instrument when it detects from the status data that the status of the energised instrument changed from being energised to not being energised or vice versa, or when it detects that the waveform of the electrical current supplied to the energised instrument changes.

As described above, the status data may comprise information on the status of the endoscope, such as whether the endoscope in a cleaning state or whether the operator is performing a white balance on the imaging system. In these cases, the augmentation system 500 (e.g. event detector 504) may be configured to determine that an instrument event has occurred if the augmentation system 500 (e.g. event detector 504) detects from the endoscope status information that the endoscope was in an endoscope cleaning state or that the white balancing was performed on the imaging system. Where the status data does not comprise information on the status of the endoscope, the augmentation system 500 (e.g. event detector 504) may be configured to automatically detect that the endoscope was in a cleaning state or that a white balance was performed on the imaging system from other status data. For example, the augmentation system 500 (e.g. event detector 504) may be configured to detect that the endoscope was in a cleaning state or that a white balance was performed on the imaging system when the augmentation system 500 (e.g. event detector 504): identifies a pattern of particular forces on the endoscope; identifies the position of the tip of the endoscope is outside the patient; identifies from a video of the operating theatre that the endoscope was cleaned or white balancing was performed; and/or identifies a combination thereof.

As described above, the status data may comprise information on the position and/or movement of the endoscope. Where the endoscope is attached to a robot arm and controlled by an operator at the operator console the endoscope position and/or movement information may be generated, for example, by position and/or torque sensors on the robot arm. In these cases, the augmentation system 500 (e.g. event detector 504) may be configured to detect that an instrument event has occurred when it detects from the position and/or movement information that the size (i.e. magnitude) or frequency of the endoscope movement has fallen outside a range.

As described above, in some cases the surgical robot system 502 may comprise a plurality of robot arms each of which may have an instrument attached thereto, and the operator (e.g. surgeon) may be able to selectively control one or more of the robot arms and the instruments attached thereto from the operator (e.g. surgeon) console. The operator may be able to select, via the operator console, which robot arms and thus which instruments are to be controlled by the operator by linking the input devices (e.g. hand controllers) to specific instruments. The instruments that are being controlled by the operator console at any one time may be referred to as the 'active' instruments. In these cases, the status data may comprise information that indicates which instruments were active at which points during the task (this may be referred to as the active instrument information). In these cases, the augmentation system 500 (e.g. event detector 504) may be configured to detect that an instrument event has occurred when the augmentation system 500 (e.g. event detector 503) detects from the active instrument information that one or more of the active instruments has changed. By detecting active instrument changes and augmenting the endoscope video which such information allows the endoscope video to include a record of the active instruments during the task.

In some cases, the augmentation system 500 (e.g. event detector 504) may be configured to additionally, or alternatively, detect collision events. Collision events may include, but are not limited to, a collision between robot arms of the surgical robot system 502, a collision between instruments attached to different robot arms of the surgical robot system 502, and a collision between a robot arm of the surgical robot system 502 and an instrument attached to another robot arm of the surgical robot system 502.

As described above, in some cases the status data may comprise data or information indicating the position and/or motion of the robot arm(s) and/or the instruments attached thereto. In these cases, the augmentation system 500 (e.g. event detector 504) may, for example, be configured to detect that a collision event has occurred (i.e. that a robot arm or instrument has collided, with another robot arm or instrument) based on the data or information indicating the position and/or motion of the robot arms and/or instruments. For example, the augmentation system 500 (e.g. event detector 504) may be configured to determine that a collision occurred between arms, between instruments, or between an arm and an instrument by, for example, (i) determining or estimating the position of the arms and/or instruments from the position and/or motion data and determining that the positions of one or more instruments and/or one or more arms are the same or are substantially similar; or (ii) determining from the position and/or motion information (e.g. torque data) that equal and opposite forces have been detected on two of the arms and/or instruments as described in the Applicant's UK Patent Application No. 1810754.0 which is herein incorporated by reference.

In some cases, the augmentation system 500 (e.g. event detector 504) may be configured to additionally, or alternatively, detect task events. Task events may include, for example, a change in the step of the task being performed. For example, the task (e.g. surgery) may be associated with a predetermined set of steps, all or a portion of which may be performed during the task and the augmentation system 500 (e.g. event detector 504) may be configured to detect that an event has occurred when it detects, from the status data, a change in the step of the task that is being performed. Automatically identifying the steps of the tasks that are being performed and augmenting the endoscope video with this information may allow the endoscope video to be automatically segmented based on the steps of the task. This may allow a user to easily identify the portions of the endoscope video that relate to particular steps of the task.

As described above, in some cases the status data may comprise information explicitly identifying which steps of the tasks were performed and when (which may be referred to herein as step identifying information). For example, as described above, the operator (e.g. surgeon) or other user (e.g. other operating team member) may be able to manually indicate, during the task, which steps of the task are being performed. In these cases, the augmentation system 500 (e.g. event detector 504) may be able to identify a change in the step of the task from the step identifying information. Where information explicitly identifying the steps of the task is not received as part of the status data the augmentation system 500 (e.g. event detector 504) may be configured to dynamically detect the steps of the task from other status data. For example, the augmentation system 500 (e.g. event detector 504) may be configured to detect the steps of the task based on patterns detected in the status data that match patterns in the status data for previously performed tasks. In particular, the augmentation system 500 (e.g. event detector 504), or another computing-based device, may be configured to analyse the status data related to previously performed tasks of the same type as the current task (e.g. status data related to the same surgical procedure or the same type of surgical procedure); identify a common set of steps in that task based on the analysis; and generate a map that links the identified steps. In some cases, the analysis may comprise at least analysing the endoscope video.

In other cases, the augmentation system 500 (e.g. event detector 504), or another computing-based device, may be provided with the status data for one or more previously performed tasks which has been manually divided into segments associated with the steps of the task and the augmentation system 500 (e.g. event detector 504), or other computing-based device, may identify characteristics or features of the status data associated with each step. For example, each step may be characterized by, for example, one of more of the following features: instrument type(s), robot arm movements and/or the hand controller movements. For example, the augmentation system 500 (e.g. event detector 504), or other computing-based device, may be configured to receive status data of a previously performed task in which the segment of the status data corresponding to a suturing step is identified as such. The augmentation system 500 (e.g. event detector 504), or other computing-based device may then analyse the portion of the status data identified as corresponding to a suturing step and identify features such as—a needle driver instrument being attached to two of the robot arms; the operator making repetitive small curved motions with the hand controllers (and thus end effectors); and high forces being exerted on the end effector and the end effector jaws. The characteristics and/or features of a step can then be used to identify that step from the status data for subsequent tasks. In some cases, the augmentation system 500 (e.g. event detector 504), or other computing-based device, may be able generate, from a single set of status data (i.e. status data relating to a single previously performed task) characteristics or features that sufficiently describe a task step so that it can be identified in another set of status data (i.e. status data related to another task). In other cases, the augmentation system 500 (e.g. event detector 504), or other computing-based device, may require multiple sets of status data to generate characteristics or features that sufficiently describe a task step so that it can be identified in another set of status data.

An example set of steps for a robot-assisted surgical procedure which may be automatically detectable by the augmentation system 500 (e.g. event detector 504) is shown in Table 1. A robot-assisted surgical procedure may include all, or only a portion of (i.e. a subset of) these steps.

TABLE 1

| Task Steps |
| --- |
| Trocar insertion |
| Instrument insertion |
| Moving organs/tissue out of the way |

TABLE 1-continued

| Task Steps |
| --- |
| Tissue dissention |
| Arrival at target organ |
| Isolation of blood supply |
| Transection of organ |
| Anastomosis/organ closure |
| Specimen retrieval |
| Haemostasis |
| Target closure/proximation |
| Instrument removal |
| Trocar/port removal |
| Wound closure |

In many cases, each task has a predefined set of steps which may be performed during the task and there only a few possible combinations of the steps which may occur. In these cases, once the augmentation system 500 (e.g. event detector 504) has detected a particular step there are typically a fairly limited number of steps that can occur after that step. This may ease the burden on the augmentation system 500 (e.g. event detector 504) in detecting the steps of the task. It may also allow the augmentation system 500 (e.g. event detector 504) to detect when there has been a deviation from the expected set of steps (e.g. when a step not in the list of expected steps is performed, or when a step in the list of expected steps is performed out of order). As described below, when the augmentation system 500 (e.g. event detector 504) detects that there has been a deviation from the expected set of steps the augmentation system 500 (e.g. event detector 504) may be configured to detect an emergency event.

In some cases, the augmentation system 500 (e.g. event detector 504) may be configured to additionally, or alternatively, detect patient events. Patient events may include one or more of the vital signs or one or more other health metrics of the patient falling outside a range; and/or a one or more vital signs and/or other health metrics of the patient changing (e.g. by more than an specific amount).

As described above, in some cases the status data may include patient health information or data that indicates the status of one or more of the patient's vital signs and/or one or more other health metrics during the task. In these cases, the augmentation system 500 (e.g. event detector 504) may be configured to detect a patient event when the patient health information or data indicates that one or more of the patient's health metrics (e.g. vital signs) have fallen outside a range. The range may vary between health metrics (e.g. there may be a different range for respiration rate and heartrate).

In some cases, the ranges may be predetermined. In other cases, the ranges may be learned from the status data for previously performed tasks. For example, the augmentation system 500 (e.g. event detector 504), or another computing-based device, may identify, from the status data of previously performed tasks, the level of the different health metrics just prior to a negative outcome occurring and generate the ranges from the identified levels (e.g. a range that encompasses the lowest and highest identified levels may be selected). The ranges may be determined across all tasks, or different ranges may be determined for different tasks (i.e. different surgical procedures). For example, it may be determined from the status data for previously performed tasks that a heartrate in the range of X to Y is normal for surgery type A, but it is not normal for surgery type B.

In some cases, the augmentation system 500 (e.g. event detector 504) may be configured to additionally, or alternatively, detect operator (e.g. surgeon) events. Operator (e.g. surgeon) events may include, but are not limited to, one or more of: the operator's (e.g. surgeon's) vital signs and/or other health metrics falling outside a range; one or more of the operator's (e.g. surgeon's) vital signs and/or other health metrics changing (e.g. by more than a specific amount); the grip force exerted by the operator (e.g. surgeon) one or more of the input devices (e.g. hand controllers) changing (e.g. by more than a specific amount); and/or the push force exerted by the operator (e.g. surgeon) on one or more of the input devices (e.g. hand controllers) changing (e.g. by more than a specific amount). For example, the augmentation system 500 (e.g. event detector) may be configured to detect an operator event has occurred if the operator's blood pressure is outside a certain range; or if the operator's heartrate is outside a certain range and the grip force exerted by the operator exceeds a specific threshold/amount.

As described above, in some cases the status data may include operator (e.g. surgeon) health information or data that indicates the status of one or more of the operator's (e.g. surgeon's) vital signs and/or one or more of the operator's (e.g. surgeon's) other health metrics during the task. In these cases, the augmentation system 500 (e.g. event detector 504) may be configured to detect an operator event when the operator health information or data indicates one or more of the operator's health metrics (e.g. vital signs) have fallen outside a range or have changed more than a specific amount. The range and/or specific amount may vary between health metrics (e.g. there may be a different range for respiration rate and heart rate), operators and/or tasks.

In some cases, the ranges and/or specific amounts may be learned from the status data for previously performed tasks. For example, the augmentation system 500 (e.g. event detector 504), or another computing-based device, may identify, from the status data of previously performed tasks, the level of the different health metrics of the operator just prior to a negative event (e.g. a negative event related to the operator or the patient) and generate the ranges from the identified levels (e.g. a range that encompasses the lowest and highest identified levels may be selected). The ranges may be determined for all operators or different ranges may be determined for different operators. For example, it may be determined from the status data for previously performed tasks that a heartrate in the range of X to Y is normal for one operator but is not normal for another operator.

As described above, in some cases, the status data may include hand controller grip information which describes the gripping force applied to one or more of the hand controllers by the operator. In these cases, the augmentation system 500 (e.g. event detector 504) may be configured to detect an operator event when the augmentation system 500 (e.g. event detector 504) detects from the hand controller grip information that the grip force has changed (or changed by more than a specific amount).

As described above, in some cases, the hand controller may be mounted on parallelogram linkages via gimbals and the status data may comprises position and/or torque data that indicates the position and/or torque of the joints of the linkage and/or gimbal. In these cases, the augmentation system 500 (e.g. event detector 504) may be configured to determine the push force exerted by the operator on one or more of the input devices (e.g. hand controllers) from the position and/or torque linkage and/or gimbal information and detect that an operator event has occurred when the augmentation system 500 detects that the push force has changed (or has changed more than a specific amount).

In some cases, the augmentation system 500 (e.g. event detector 504) may be configured to additionally, or alternatively, detect performance events. Performance events are events that relate to the performance of the operator (e.g. surgeon) in performing the task (or portion of the task) and may include, but are not limited to, the performance of the operator (e.g. surgeon) has fallen below an acceptable level, and/or the performance of the operator (e.g. surgeon) has changed (or changed more than a specific amount).

In some cases, the augmentation system 500 (e.g. event detector 504) may be configured to detect that the performance of the operator (e.g. surgeon) has fallen below a threshold by comparing the status data for the task to the status data for previously performed tasks (e.g. tasks of the same type). For example, the augmentation system 500 may have access to a data repository in which the status data for previously performed tasks is stored and in which the performance of the operator (e.g. surgeon) has been assessed or identified (e.g. the performance may be ranked on a scale such as, but not limited to a scale from 1 to 10); and the status data may be compared to the status data stored in the repository to determine the performance level of the operator (e.g. surgeon) for the task.

In some cases, the augmentation system 500 (e.g. event detector 504) may be configured to determine the performance level of the operator (e.g. surgeon) for the task by comparing one or more performance metrics of the operator (e.g. surgeon) to the performance metrics of the operators (e.g. surgeons) for the previously performed tasks. For example, the augmentation system 500 (e.g. event detector 504) may be configured to determine the performance level (e.g. determine the level from 1 to 10 for example) of the operator at a plurality of points in time during the task based on the performance metrics and the augmentation system 500 (e.g. event detector 504) may detect a performance event if the performance level changes or if the performance level falls outside an acceptable range. In some cases, the performance metrics may include one or more of: the path taken by a robot arm or instrument in performing a task or step of the task; the smoothness of the movement of the robot arm and/or instrument in performing a task or step of the task; the time taken to perform the task or step of the task; and/or the amplitude or frequency of the movement of the robot arm.

As described above, in some cases the status data may comprise information describing the position and/or movement of the arm(s) and/or instrument(s) of the surgical robot system 502. In these cases, the augmentation system 500 (e.g. event detector 504) may be configured to determine the path of the robot arm and/or instrument from the information describing the position and/or movement of the arm(s) and/or instrument(s). Once the path taken has been identified the augmentation system 500 (e.g. event detector) may be configured to assess the performance of the user by comparing the path taken to the "best" or "optimum" path for that task or step of the task. The "best" path may be determined from the status data for previously performed tasks. For example, the augmentation system 500, or another computing-based device, may be configured to determine a "best" path from status data for previously performed tasks in which the path has been ranked. In addition to all of the sources of status data described above, the status data for previously performed tasks may also comprise outcome data. As is known to those of skill in the art outcome data is information about the results (e.g. success/failure) of a surgery. In some cases, the closer the path taken is to the "best" or "optimum" path the better the performance and the further away the path is from the "best" or "optimum" path the poorer the performance.

The augmentation system 500 (e.g. event detector 504) may also be able to measure the smoothness of the path based on whether the path has smooth curves or jagged edges and the augmentation system 500 (e.g. event detector 504) may be configured to assess the performance of the operator based on the number of smooth curves and/or the number of jagged edges, for example.

As described above, in some cases, the status data may comprise information explicitly identifying the task and/or step(s) of the task that were performed. In other cases, the augmentation system 500 may be able to dynamically identify the task and/or step of the task based on other status data. In either case, the augmentation system 500 (e.g. event detector 504) may be configured to determine the time taken to perform the task or a step of the task by measuring the time between tasks or between steps of the task. The augmentation system 500 (e.g. event detector 504) may be able to assess the performance of the operator by comparing the time taken to complete the task or step of the task to the time taken (as generated from the status data) to complete the same task or same step during previously performed tasked.

As described above, in some cases the status data may comprise information describing the position and/or movement of the input devices (e.g. hand controllers). In these cases, the augmentation system 500 may be configured to determine from the hand controller position and/or movement data the amplitude (e.g. magnitude) and frequency of movement of the hand controllers. The augmentation system 500 may then be configured to assess the performance of the operator based on the measured amplitude and frequency of movement. Specifically, large and/or lots of changes in movement may indicate poor performance whereas small infrequent movements may indicate good performance.

For example, the augmentation system 500 (e.g. event detector 504) may be configured to convert the hand controller position and/or movement data from the time domain to the frequency domain (via a Fourier transform, for example) and identify patterns in the frequency domain that indicate an event occurred. For example, if the augmentation system 500 detects a lot of low frequency components in the frequency domain this may indicate fatigue or intoxication; whereas lots of high frequency components in the frequency domain may indicate a high level of shakiness or panicked movement. In some cases, there may be acceptable ranges for the low frequency and high frequency components and if either or both fall outside the corresponding acceptable range the augmentation system 500 (e.g. event detector 504) may be configured to determine that a performance event has occurred.

In some cases, the augmentation system may be configured to determine a single operator performance score, or descriptor based on a plurality of performance criteria. In other cases, the augmentation system 500 (e.g. event detector 504) may be configured to determine multiple operator performance scores, each based on a different performance criterion. The augmentation system 500 (e.g. event detector 504) may be configured to determine that a performance event has occurred if any of the performance criteria have fallen below an acceptable level or if any of the performance criteria change (by, for example, at least a specific amount).

In some cases, the augmentation system 500 (e.g. event detector 504) may be configured to additionally, or alternatively, detect emergency events. Emergency events are events that indicate an emergency has occurred or is likely to have occurred during the task. The augmentation system 500 (e.g. event detector 504) may be configured to detect an emergency event when the augmentation system 500 detects: one or more of the individuals present for the task (e.g. one or more of the surgical team) spoke in a raised voice; one or more of the individuals present for the task (e.g. one or more of the surgical team) spoke a warning word or phrase; a sudden movement by a surgical robot arm; and/or a deviation or departure from the predetermined steps of the task.

As described above, in some cases the status data may include a video and/or audio recording of the room (e.g. operating room) in which the task is performed. In these cases, the augmentation system 500 (e.g. event detector 504) may be configured to detect an emergency event when the augmentation system 500 (e.g. event detector 504) detects from the video and/or audio recording that an individual in the room has spoken in a raised voice. Specifically, if an individual is speaking in a raised voice it may indicate that there is some friction between individuals in the room/theatre and/or that there is an issue or problem in the room/theatre. The augmentation system 500 (e.g. event detector 504) may be able to detect a raised voice using any known speech analysis technique.

Where the status data includes a video and/or audio recording, the augmentation system 500 (e.g. event detector 504) may also, or alternatively, be configured to detect an emergency event when the augmentation system 500 (e.g. event detector 504) detects from the video and/or audio recording that an individual in the room has spoken a warning word or phrase (i.e. a word or phrase that indicates that there may be a problem). The augmentation system 500 (e.g. event detector 504) may be configured to detect warning words and/or phrases in the video and/or audio recording using any known speech recognition or analysis technique. The list of warning words and/or phrases may be pre-loaded into the augmentation system 500 (e.g. event detector 504) prior to starting the analysis. In some cases, the list of warning words and/or phrases may be learned from the status data of previously performed tasks. For example, the augmentation system 500 (e.g. event detector 504), or another computing-based device, may identify, from the status data of each of a plurality of previously performed tasks, any words or phrases spoken a certain period of time before a negative outcome and generate a list of identified words or phrases that are common between a certain number of previously performed tasks.

It will be evident to a person of skill in the art that this is an example set of events that the augmentation system 500 (e.g. event detector 504) may be capable of detecting and that in other examples the augmentation system (e.g. event detector 504) may be configured to detect additional events, only a subset of events or different events. For example, other events that the augmentation system 500 (e.g. event detector 504) may be able to detect include, but are not limited to, pressure drops in the insufflation equipment.

In some cases, once a set of events has been identified from the status data the augmentation system 500 (e.g. event detector 504) may be configured to automatically identify additional events based on patterns of events. For example, certain patterns of events may indicate another event has occurred. The patterns of events that indicate a particular event has occurred may be learned (e.g. from the status data for previously performed tasks—the previously performed tasks may be the same task as the current task, a similar set of tasks to the current task, or a different set of tasks relative to the current task).

In some cases, the augmentation system 500 (e.g. event detector 504) may be able to detect a predetermined set of events from the status data. The predetermined set of events that the augmentation system 500 (e.g. event detector 504) is able to detect from the status data may be based on the types of status data received and/or one or more other criteria. In some cases, the augmentation system 500 may be configured to only detect a subset of the predetermined set of events that it is capable of detecting. For example, a user may be able to configure the augmentation system 500 (e.g. event detector) to only detect a subset of the predetermined set of events. This may be useful when, for example, the user is looking for something specific in the endoscope video. For example, there may be a user interface (e.g. a graphical user interface (GUI)) linked to the augmentation system 500 (e.g. event detector 504) that allows a user to configure the augmentation system 500. The user interface may, for example, present the predetermined set of events supported by the augmentation system 500 to the user and the user may select which of the supported events are to be detected by the augmentation system (e.g. event detector 504).

Alternatively, or in addition, to a user being able to manually select which events the augmentation system 500 (e.g. event detector 504) is to detect, the augmentation system 500 (e.g. event detector 504) may be configured to automatically select the events that are to be detected based on the user that is logged into the augmentation system 500. For example, in some cases, to generate an augmented endoscope video based on the status data a user may have to log in or otherwise authenticate themselves with the augmentation system 500 and the events that are detected by the augmentation system 500 (e.g. event detector 504) are based on, for example, the privileges of the user. For example, the operator that performed the task may be able to access more events than another operator (e.g. surgeon). For example, the operator that performed the task may be able to see performance events whereas another operator (e.g. surgeon) may not be able to see performance events for that particular task. As described in more detail below, instead of the augmentation system 500 (e.g. event detector 504) being configured to only detect a subset of the predetermined set of events from the status data, the augmentation system 500 may be configured to detect all of the predetermined set of events and the events that are available to the user when the augmented video is viewed may be configurable and/or based on user privileges.

In some cases, for each event detected from the status data, the augmentation system 500 (e.g. event detector 504) may generate event information which is used to augment the endoscope video. The event information may include, but is not limited to, an event identifier which identifies the detected event, event start time which identifies when the event started, and optionally, an event duration or an event end time that indicates when the event ceased (in the cases where the event has a duration). The event identifier may be a name or a number that identifies the event that was detected. In some cases, there may be a predetermined set of events that can be detected which are listed in, for example, a lookup table with a number and a text description. The start time and/or end time may be an absolute time (e.g. 3:45 pm) or may be a relative time (e.g. 35 minutes after the task started).

Once the augmentation system 500 (e.g. event detector 504) has analysed the status data to identify events that occurred during the task, the method 800 proceeds to block 808 where the endoscope video is augmented. It is noted that although in the method 800 of FIG. 8 the event detector analyses the status data to identify all events that occurred during the task and then the method 800 proceeds to block 808 for augmentation of the endoscope video, in other example methods the endoscope video may be augmented on a per event basis. In other words, in other cases the endoscope video may be augmented as soon as an event is detected instead of having to wait until all of the events are detected.

At block 808, the augmentation system 500 (e.g. augmenter 506) generates an augmented endoscope video by augmenting the endoscope video received in block 802 with information, for each event detected in block 806, that identifies the detected event and the time at which the event occurred with respect to the endoscope video. As described above, in some cases the information added to the endoscope video may take the form of a marker which is placed at the relevant time of the endoscope video (e.g. when the event started, or over the duration of the event). The information or marker may be visible to the user when the augmented endoscope video is subsequently played or viewed, via, for example, a media player. In some cases, the marker may take the form of a bookmark that allows a user to easily jump to a certain point of the endoscope video when the augmented endoscope video is played or viewed via, for example, a media player. For example, when the user launches the augmented endoscope video in a media player the user may be presented with a list of bookmarks in the video which represent the detected events and the user can go directly to one of the points identified by a bookmark by selecting the bookmark. In some cases, the information (e.g. marker) relating to a particular event may be included in the metadata that forms part of or is associated with the endoscope video.

For example, Table 2 shows a list of events that may have been detected by the augmentation system 500 (e.g. event detector 504) in block 806. It will be evident to a person of skill in the art that these are example events, start times, end times, and durations and that other events with other state times, end times, and durations may be detected.

TABLE 2

| Type of Event | Event Identifier | Start of Event | End of Event |
| --- | --- | --- | --- |
| Task Event | Suturing Step | Minute 25 | Minute 45 |
| Instrument Event | Instrument Change - Needle Driver attached to Arm 0 | Minute 25 | Minute 30 |
| Instrument Event | Instrument Change - Needle Driver attached to Arm 1 | Minute 30 | Minute 35 |
| Performance Event | Change in Performance - Performance Level 7 | Minute 65 | — |

Figure 10:
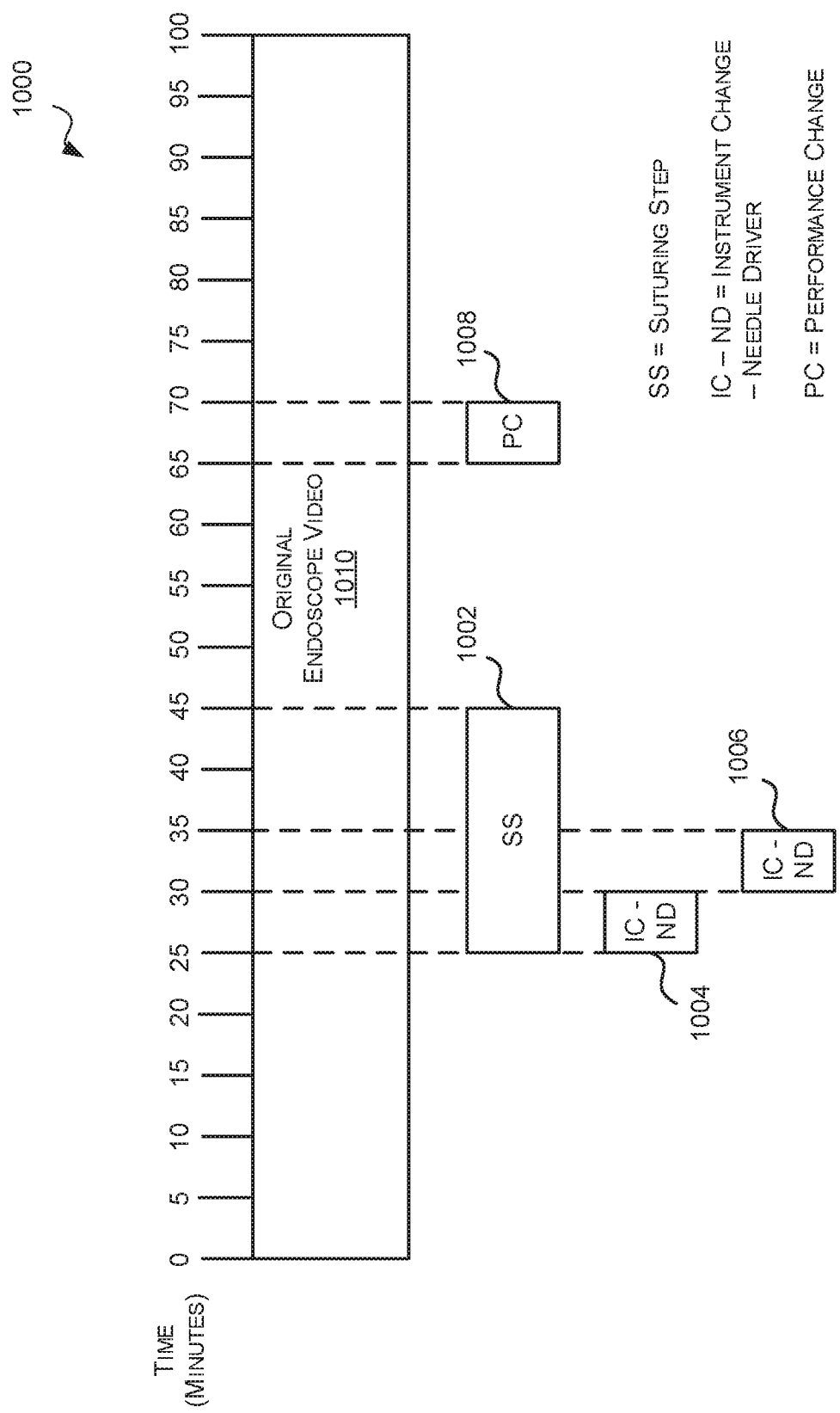
FIG. 10 is a schematic diagram of an example augmented endoscope video.

FIG. 10 is an example augmented endoscope video 1000 that has been augmented based on the events shown in Table 2 having been detected by the augmentation system 500 (e.g. event detector) in block 806. It can be seen from FIG. 10 that in this example the augmentation system 500 (e.g. augmenter 506) added one marker 1002, 1004, 1006, 1008 for each of the identified events to the original endoscope video 1010 to generate the augmented endoscope video 1000. Specifically, the augmentation system 500 (e.g. augmenter 506) added a first marker 1002 that indicates that a suturing step occurred between minute 25 and minute 45; a second marker 1004 that indicates that a needle driver instrument was attached to robot arm 0 between minute 25 and minute 30; a third marker 1006 that indicates that a needle driver instrument was attached to robot arm 1 between minute 30 and minute 35; and a fourth marker 1008 that indicates that the performance of the operator changed to level 7 at minute 65. It will evident to a person of skill in the art that this is only an example of how an endoscope video may be augmented and that in other examples the endoscope video may be augmented in a different manner.

Figure 11:
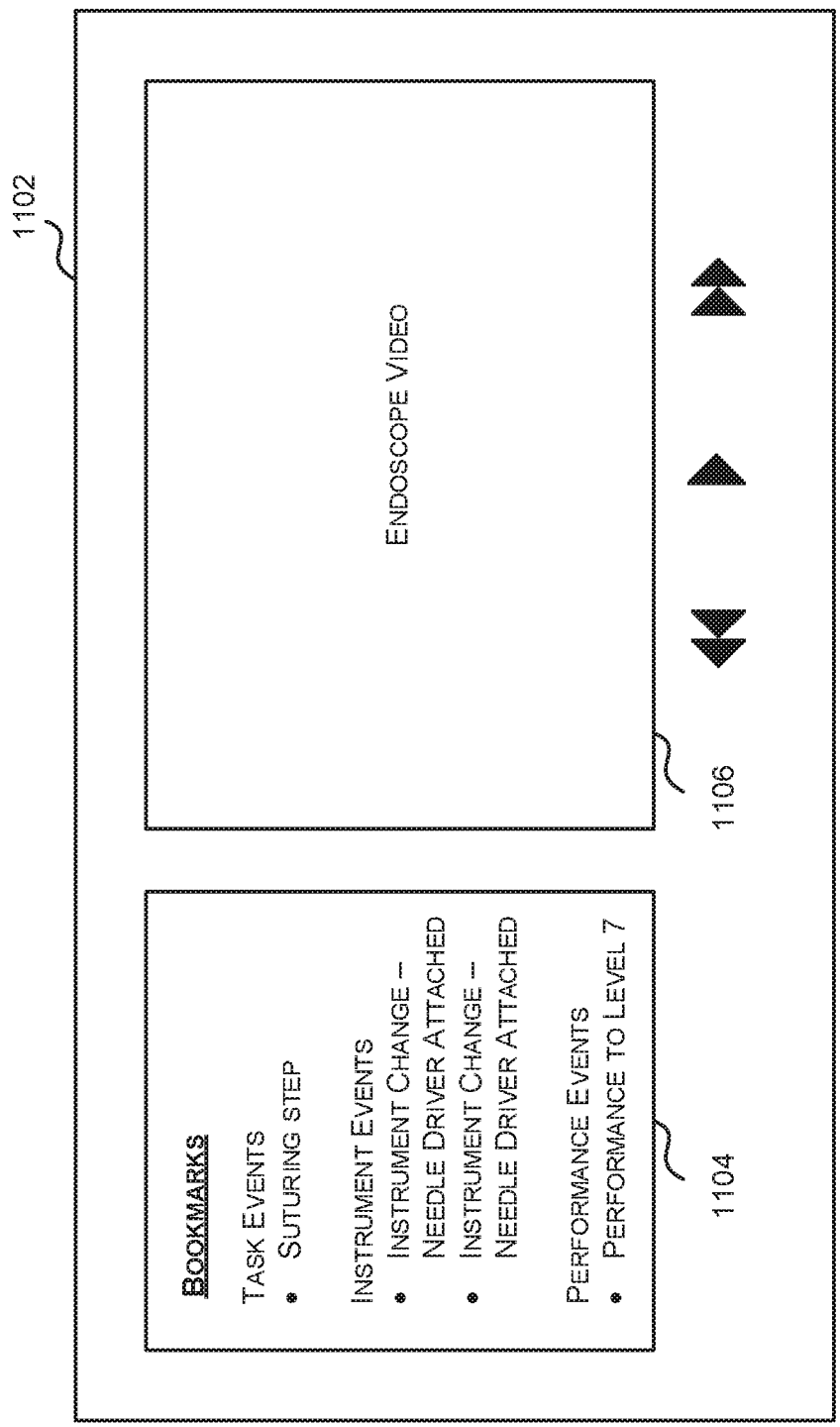
FIG. 11 is a schematic diagram of an example augmented endoscope video being viewed on a media player.

Once the augmented endoscope video has been generated the augmented endoscope video may be stored in memory of the augmentation system 500 or in memory of another device for later use. For example, the stored augmented endoscope video may be subsequently viewed or played using, for example, a media player to review the operator's performance, to teach operators how to perform the procedure etc. The information or markers added to the augmented endoscope video may be viewable by a user when the augmented endoscope is viewed or played. In particular, in some cases, the information or markers may be presented as bookmarks. For example, as shown in FIG. 11, when a user views the example augmented endoscope video 1000 of FIG. 10, via, for example, a media player 1102 the user may be presented with a list of the bookmarks 1104 (or a menu of bookmarks) alongside the endoscope video 1106. For example, in FIG. 11 there is a bookmark for each event detected in Table 2—a bookmark for the suturing step, a bookmark for each instrument change, and a bookmark for the change in performance level. The user can then automatically move to a particular portion of the endoscope video 1106 by selecting one of the bookmarks 1104. In some cases, as shown in FIG. 11, the bookmarks 1104 may be presented to the user in groups, based on, for example, type or time. However, it will be evident to a person of skill in the art that this is an example only and that the bookmarks may be presented to the user in another way.

In some cases, in addition to the information or marker added to the endoscope video for each detected event being presented to the user as a bookmark, the information added to the endoscope video for the detected events may be presented to the user as the endoscope video is being played back. For example, the augmented endoscope video may be augmented so that when the video is played back a banner at the top, bottom or side of the screen displays event information—i.e. it displays information about the detected events at the appropriate or relevant time of the endoscope video.

In some cases, the information or markers that are viewable when an augmented endoscope video is viewed or played using, for example, a media player may be configurable. For example, the user of the augmented endoscope video may be presented with a list of events that were tagged in the augmented endoscope video and the user may be able to select which of those events are to be viewable. The user may be able to select individual events or types of events. For example, the user may be able to select all instrument events and/or all task events; or some instrument events and/or some task events. In some cases, the information or markers that are viewable when the augmented endoscope video is viewed or played may be based on the user viewing the augmented endoscope video. For example, in some cases, to view an augmented endoscope video the user may have to login to, or otherwise be authenticated with, an endoscope video viewing system. In these cases, the information or markers that are viewable when an augmented endoscope video is viewed or played may be determined based on the privileges associated with the user playing the video. For example, the operator that performed the task may be able to view all of the information or markers whereas other users may only be able to view a subset of the information or markers. For example, other users may not be able to view any information or markers related to performance events.

In some cases, in addition to being configured to automatically augment the endoscope video with information or markers that identify events that occurred during the task, the augmentation system 500 may also be configured to generate a three dimensional (3D) virtual reality (VR) reconstruction of the instruments and their positions and/or movement from the status data. The augmentation system 500 may then synchronise and link the augmented endoscope video with the 3D VR reconstruction of the instruments so that when the endoscope video is viewed or played the 3D VR reconstruction can be viewed alongside the augmented endoscope video. For example, as described above, in some cases the status data may comprise information describing the position and/or movements of the robot arm(s) and/or the instruments attached thereto during the task, and information describing the instruments attached to each robot arm during the task. In these cases, the augmentation system 500 may be configured to determine the position and movement of the instruments from the robot arm/instrument position/movement information. Once the position and movement of the instruments has been identified the movements may be mapped to 3D models of the relevant instruments based on the type of instrument that was attached to each arm (as identified by the instrument information of the status data). Once the movements are mapped to 3D models the 3D models can be merged to form a 3D VR reconstruction of the instruments during the task. The 3D VR reconstruction can then be time synchronised and linked to the augmented endoscope video. In some cases, the perspective or view of the instruments in the 3D VR reconstruction may be configurable (i.e. the user may be able to set or configure the viewpoint). This may allow the user to view the instrument from a different viewpoint than from the viewpoint of the endoscope. In some cases the viewpoint may be dynamically reconfigurable during playback. Specifically, the 3D VR reconstruction may allow the user to adjust the viewpoint during playback or viewing.

In some cases, in addition to being configured to automatically augment the endoscope video with information or markers that identify events that occurred during the task and the time or period at which they occurred with respect to the endoscope video, the augmentation system 500 may also be configured to link the augmented endoscope video to all or a portion of the status data in a manner that links the identified events, not only to the relevant portion of the endoscope video, but also to the relevant portions of all or a portion of the status data. For example, the augmented endoscope video may be linked to all or only a subset of the data streams that form the status data. For example, if the status data comprises a patient heartrate data stream and a surgical robot arm position information data stream the augmented endoscope video may be linked to either or both data streams. The linked augmented endoscope video and status data may be referred to as the augmented combined data.

Figure 12:
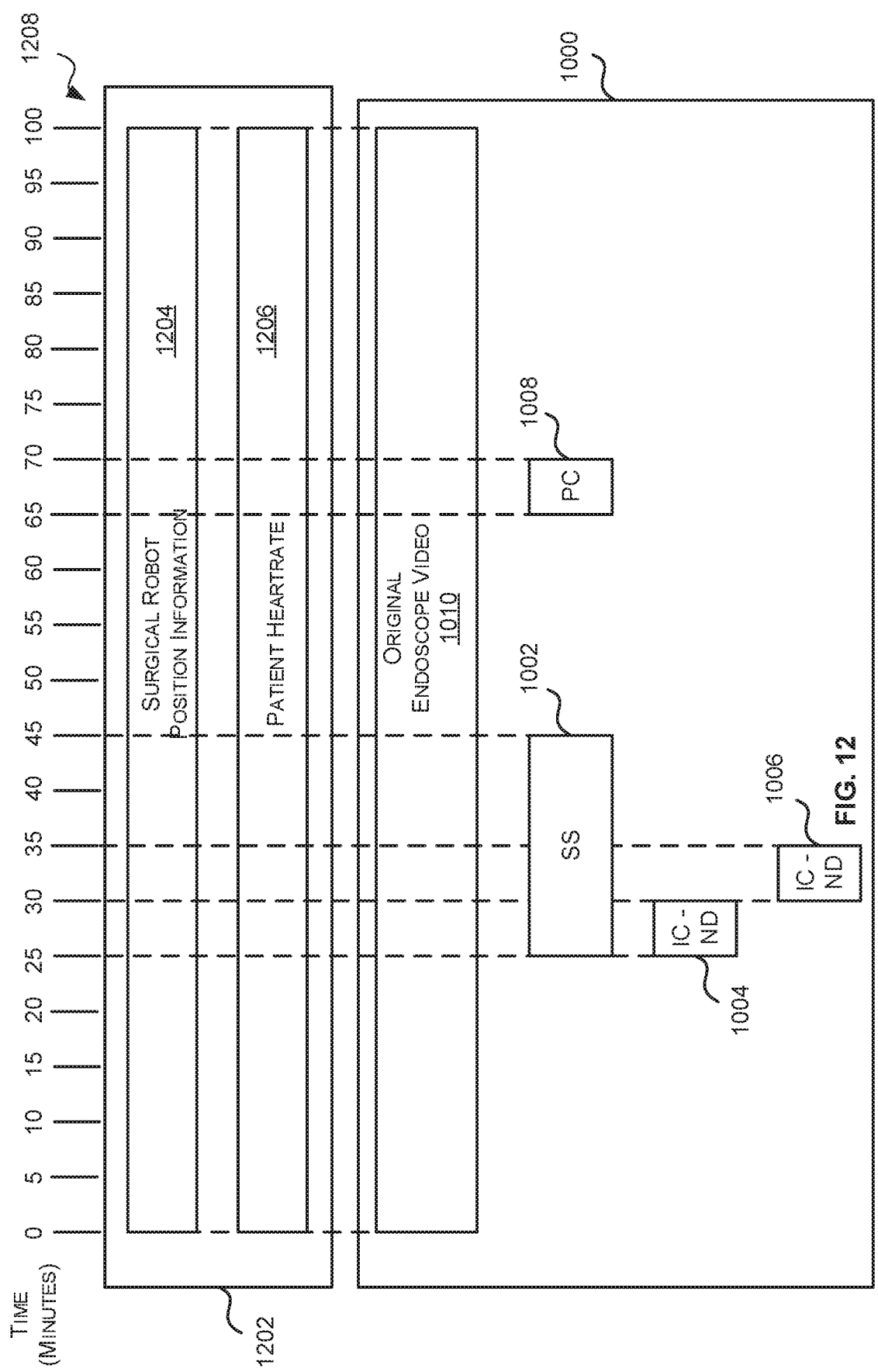
FIG. 12 is a schematic diagram of an example augmented endoscope video linked to the corresponding status data.

As described above, the status data is time synchronised with the endoscope video via, for example, common timestamps or a common timeline. Accordingly, the augmented combined data may be generated by linking the augmented endoscope video with all or a portion of the status data so that the corresponding portions of the endoscope video and the status data are aligned or linked. For example, FIG. 12 illustrates the example augmented endoscope video 1000 of FIG. 10 linked to the corresponding status data 1202 so that the corresponding portions of the endoscope video 1000 and the status data 1202 are aligned or linked. In this example the status data 1202 comprises two data streams—a patient heartrate data stream 1206 and a surgical robot position information data stream—and both data streams are linked to the augmented endoscope video 1000. This means that, for example, the heartrate data and surgical robot position information at 30 minutes (into the task) is linked to the endoscope video at 30 minutes (into the task). However it will be evident to a person of skill in the art this is an example only and the status data 1202 may comprise any combination of the data streams described above. The linked augmented endoscope video 1000 and status data 1202 form the augmented combined data 1208.

Once the augmented endoscope video is linked to the status data to form the augmented combined data the information and/or markers in the augmented endoscope video can be used to identify the portions of the endoscope video and status data that relate to each of the identified events. In this manner the information or markers in the augmented endoscope video can be thought of as identifying time slices of the combined data that relate to the identified events. For example, the marker 1002 which identifies a suturing step identifies the portions of the endoscope video, the patient heartrate data stream and the surgical robot position information data stream that correspond to the suturing step. The markers can then be used to retrieve the data from the endoscope video and/or one or more other data streams of the status data that relate to that event. For example, there may be a system or software configured to receive the augmented combined data which is able to present to the user, based on the information or markers in the augmented combined data, a list of identified events. Then by selecting one of the events the user may be presented with the portions of the endoscope video and status data that relate to that event. The portions of the endoscope video and status data that relate to the event may be presented to the user in any suitable form. For example, by selecting a listed event the portion of the endoscope video that relates to that event may be played alongside a display of the related status data (e.g. the patient heartrate during the relevant portion may be displayed above, below, or to the side of the endoscope video as it is being played).

While it has been described above the that augmented combined data is generated by first generating the augmented endoscope video and then linking the augmented endoscope video, in other examples the endoscope video may be linked to all or a portion of the status data to generate combined data prior to the augmentation such that the augmenter 506 augments the combined data with information or markers that identify the identified events and when they occurred to generate the augmented combined data.

Figure 13:
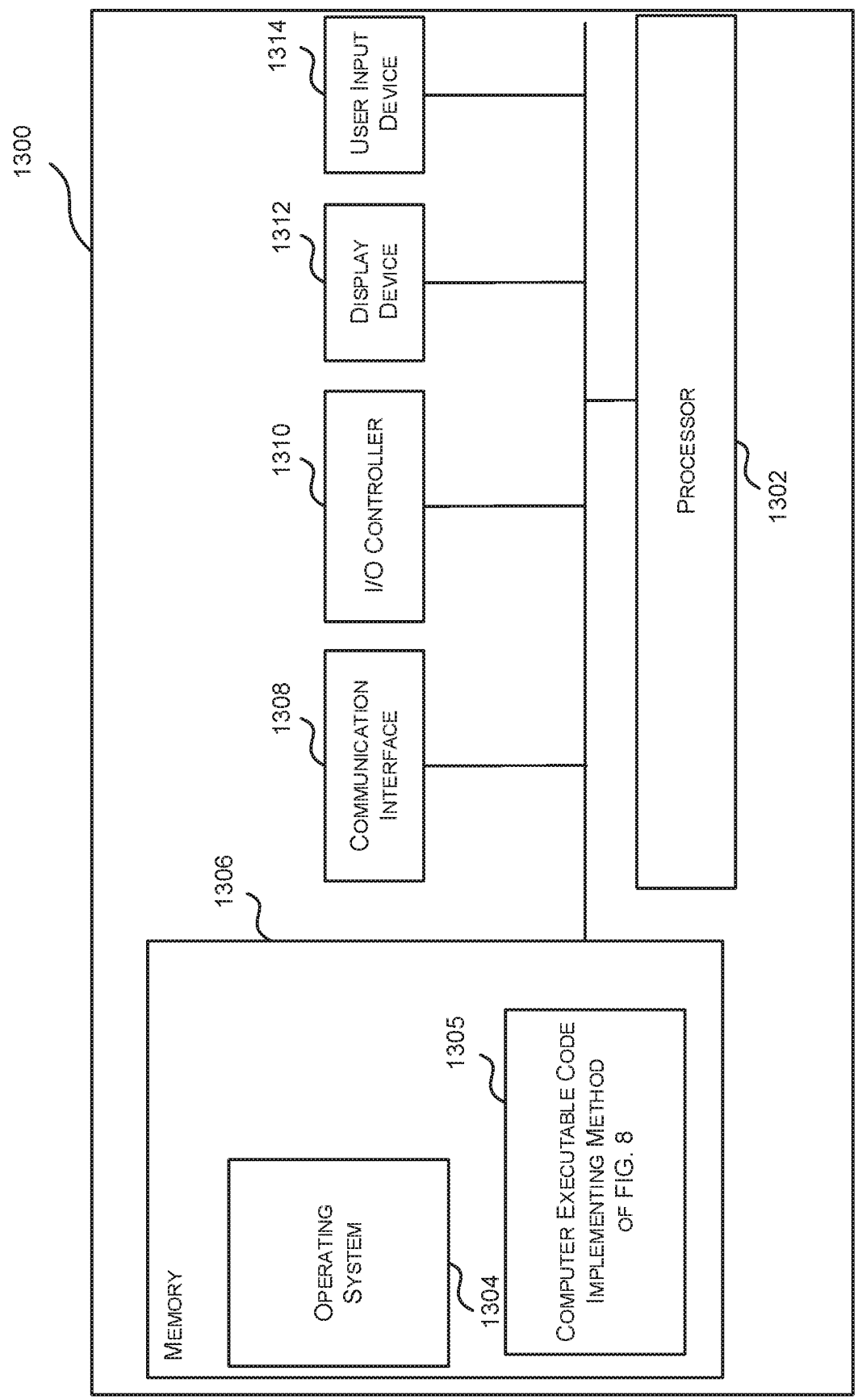
FIG. 13 is a block diagram of an example computing-based device.

Reference is now made to FIG. 13 which illustrates various components of an exemplary computing-based device 1300 which may be implemented as any form of a computing and/or electronic device, and in which embodiments of the methods and augmentation systems described herein may be implemented.

Computing-based device 1300 comprises one or more processors 1302 which may be microprocessors, controllers or any other suitable type of processors for processing computer executable instructions to control the operation of the device in order to verify a hardware design for a data transformation pipeline. In some examples, for example where a system on a chip architecture is used, the processors 1302 may include one or more fixed function blocks (also referred to as accelerators) which implement a part of the method of augmenting an endoscope video, in hardware (rather than software or firmware). Platform software comprising an operating system 1304 or any other suitable platform software may be provided at the computing-based device to enable application software, such as software 1305 implementing the method of FIG. 8, to be executed on the device.

The computer executable instructions may be provided using any computer-readable media that is accessible by computing-based device 1300. Computer-readable media may include, for example, computer storage media such as memory 1306 and communications media. Computer storage media (i.e. non-transitory machine-readable media), such as memory 1306, includes volatile and non-volatile, removable and non-removable media implemented in any method or technology for storage of information such as computer readable instructions, data structures, program modules or other data. Computer storage media includes, but is not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing-based device. In contrast, communication media may embody computer readable instructions, data structures, program modules, or other data in a modulated data signal, such as a carrier wave, or other transport mechanism. As defined herein, computer storage media does not include communication media. Although the computer storage media (i.e. non-transitory machine-readable media, e.g. memory 1306) is shown within the computing-based device 1300 it will be appreciated that the storage may be distributed or located remotely and accessed via a network or other communication link (e.g. using communication interface 1308).

The computing-based device 1300 also comprises an input/output controller 1210 arranged to output display information to a display device 1312 which may be separate from or integral to the computing-based device 1300. The display information may provide a graphical user interface. The input/output controller 1310 is also arranged to receive and process input from one or more devices, such as a user input device 1314 (e.g. a mouse or a keyboard). This user input may be used to initiate verification. In an embodiment the display device 1312 may also act as the user input device 1314 if it is a touch sensitive display device. The input/output controller 1310 may also output data to devices other than the display device, e.g. a locally connected printing device (not shown in FIG. 13).

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein. In view of the foregoing description it will be evident to a person skilled in the art that various modifications may be made within the scope of the invention.

The invention claimed is:

1. An augmentation system to generate an augmented endoscope video, the augmentation system comprising one or more processors configured to:

receive status data describing a status of a surgical robot system during a task at least partially performed by the surgical robot system, the surgical robot system comprising at least one surgical robot having a base, and an arm extending from the base to an attachment for an instrument, the arm comprising a plurality of joints whereby the configuration of the arm can be altered, the status data comprising instrument information describing at least one instrument attached to the at least one surgical robot during the task and surgical robot position information describing a movement and/or a position of the at least one surgical robot during the task;

identify one or more patterns in the status data that indicate an event occurred during the task, the one or more patterns in the status data comprising one or more patterns in the instrument information and/or one or more patterns in the surgical robot position information;

identify a suturing step in the task by identifying the one or more patterns in the instrument information and the one or more patterns in the surgical robot position information;

receive an endoscope video captured during the task, the endoscope video being time synchronised with the status data; and in response to the one or more processors identifying a pattern in the status data that indicates the event occurred, automatically augment metadata that forms part of or is associated with the endoscope video with information identifying the event and a time of the event with respect to the endoscope video.

2. The augmentation system of claim 1, wherein the information identifying the event and the time of the event is visible to a user when the augmented endoscope video is subsequently viewed by the user.

3. The augmentation system of claim 1, wherein the information identifying the event and the time of the event is selectively visible to a user when the augmented endoscope video is viewed by the user subsequent to the task.

4. The augmentation system of claim 1, wherein the information identifying the event and the time of the event is automatically viewable or not viewable to a user when the augmented endoscope video is viewed by the user subsequent to the task, based on privileges associated with the user.

5. The augmentation system of claim 1, wherein augmenting the metadata with the information identifying the event and the time of the event with respect to the endoscope video comprises adding a bookmark to the endoscope video at the time of the event that identifies the event.

6. The augmentation system of claim 1, wherein the one or more patterns in the status data comprises a plurality of patterns, each pattern corresponding to a different event, and the one or more processors are configurable to selectively identify only a subset of the plurality of patterns.

7. The augmentation system of claim 1, wherein the one or more patterns in the status data comprises a plurality of patterns, each pattern corresponding to a different event, and the one or more processors are configured to identify a subset of the plurality of patterns based on user privileges associated with a user that initiated the augmentation.

8. The augmentation system of claim 1, wherein the status data at least partially comprises data generated by the surgical robot system.

9. The augmentation system of claim 8, wherein the status data at least partially comprises data generated by one or more sources external to the surgical robot system.

10. The augmentation system of claim 1, wherein the one or more patterns in the status data are configured to identify one or more instrument events, the one or more instrument events comprising one or more of: a change in the at least one instrument attached to the arm of the surgical robot system; a change in a status of an energised instrument attached to the arm of the surgical robot system; cleaning of an endoscope attached to the arm of the surgical robot system; performing a white balance on an imaging system of the endoscope attached to the arm of the surgical robot system; a size or frequency of movement of the endoscope attached to the arm of the surgical robot system falling outside a range; and a change in the at least one instrument attached to the arm of the surgical robot system being actively controlled by the surgical robot system.

11. The augmentation system of claim 1, wherein the one or more patterns in the status data are configured to identify one or more collision events, the one or more collision events comprising one or more of: a collision between at least two surgical robot arms of the surgical robot system; a collision between at least two instruments attached to different surgical robot arms of the surgical robot system; and a collision between the arm of the surgical robot system and an instrument attached to another surgical robot arm of the surgical robot system.

12. The augmentation system of claim 1, wherein the task is a surgical procedure performed on a patient and the one or more patterns in the status data are configured to identify one or more patient events, the one or more patient events comprising one or more of: one or more vital signs or one or more other health metrics of the patient falling outside a range; and a change in the one or more vital signs and/or the one or more other health metrics of the patient.

13. The augmentation system of claim 1, wherein the surgical robot system is controlled by an operator, and the one or more patterns in the status data are configured to identify one or more operator events, the one or more operator events comprising one or more of: one or more vital signs and/or one or more other health metrics of the operator falling outside a range; a change in the one or more vital signs and/or the one or more other health metrics of the operator; a change in a grip force exerted by the operator on one or more input devices used to control the surgical robot system; and a change in a push force exerted by the operator on the one or more input devices.

14. The augmentation system of claim 1, wherein the surgical robot system is controlled by an operator, and the one or more patterns in the status data are configured to identify one or more operator performance events, the one or more operator performance events comprising one or more of: a performance of the operator in performing the task falling below an acceptable level, and a change in the performance of the operator in performing the task.

15. The augmentation system of claim 1, wherein the task comprises a plurality of steps and the one or more patterns in the status data are configured to automatically identify the one or more steps of the task from the status data.

16. The augmentation system of claim 1, wherein the one or more processors are configured to identify the suturing step in the task when the one or more processors identify from the instrument information that at least two needle drivers are attached to surgical robots and the one or more processors identify from the surgical robot position information that the surgical robots were moved in repeated circular motions.

17. The augmentation system of claim 1, wherein the system is further configured to link the augmented endoscope video and all or a portion of the status data so that the information identifying the event identifies the time the event occurred with respect to the endoscope video and the status data.

18. The augmentation system of claim 17, wherein a portion of the endoscope video and the portion of the status data relating to the identified event are retrievable from the information identifying the event.

19. A computer-implemented method of generating an augmented endoscope video, the method comprising, at one or more computing-based devices:

receiving an endoscope video captured during a task at least partially performed by a surgical robot system, the surgical robot system comprising at least one surgical robot having a base, and an arm extending from the base to an attachment for an instrument, the arm comprising a plurality of joints whereby the configuration of the arm can be altered, the status data comprising instrument information describing at least one instrument attached to the at least one surgical robot during the task and surgical robot position information describing a movement and/or a position of the at least one surgical robot during the task;

receiving status data describing a status of the surgical robot system during the task, the status data being time synchronised with the endoscope video;

identifying one or more patterns in the status data that indicate an event occurred during the task, the one or more patterns in the status data comprising one or more patterns in the instrument information and/or one or more patterns in the surgical robot position information, and a suturing step is identified in the task by identifying the one or more patterns in the instrument information and the one or more patterns in the surgical robot position information; and in response to identifying a pattern in the status data that indicates that the event occurred during the task, augmenting metadata that forms part of or is associated with the endoscope video with information identifying the event and a time of the event with respect to the endoscope video.

* * * * *